(12) United States Patent
Segal et al.

(10) Patent No.: US 8,226,587 B2
(45) Date of Patent: Jul. 24, 2012

(54) PELVIC ANCHOR BRACE AND SPINAL SUPPORT

(75) Inventors: David Segal, Jerusalem (IL); Dael Govreen-Segal, Hod Hasharon (IL)

(73) Assignee: Koala Health Accesories Ltd., Petach Tikva (IL)

( * ) Notice: Subject to any disclaimer, the term of this patent is extended or adjusted under 35 U.S.C. 154(b) by 137 days.

(21) Appl. No.: 12/400,109

(22) Filed: Mar. 9, 2009

(65) Prior Publication Data

US 2009/0254015 A1 Oct. 8, 2009

Related U.S. Application Data

(63) Continuation-in-part of application No. PCT/IL2007/001099, filed on Sep. 5, 2007.

(60) Provisional application No. 60/842,663, filed on Sep. 7, 2006, provisional application No. 60/902,047, filed on Feb. 20, 2007, provisional application No. 61/064,583, filed on Mar. 13, 2008, provisional application No. 61/136,954, filed on Oct. 16, 2008.

(51) Int. Cl.
*A61F 5/00* (2006.01)
*A61F 5/24* (2006.01)

(52) U.S. Cl. .......... 602/19; 128/95.1; 128/96.1
(58) Field of Classification Search .......... 602/32–36, 602/38, 19; 606/237, 240–242, 244; 297/353; 128/845, 873–875, 95.1, 96.1; 482/95, 96, 482/131, 143, 907

See application file for complete search history.

(56) References Cited

U.S. PATENT DOCUMENTS

| | | | | |
|---|---|---|---|---|
| 1,940,904 A * | 12/1933 | Dayton et al. | ............... | 602/19 |
| 1,987,432 A * | 1/1935 | Chesterman | ............... | 128/95.1 |
| 2,048,087 A * | 7/1936 | Wagenseil | ............... | 128/96.1 |
| 2,548,557 A * | 4/1951 | Puski | ............... | 128/96.1 |
| 2008/0262401 A1 * | 10/2008 | Wagner et al. | ............... | 602/19 |

* cited by examiner

*Primary Examiner* — Patricia Bianco
*Assistant Examiner* — Tarla Patel
(74) *Attorney, Agent, or Firm* — Graeser Associates International Inc; Dvorah Graeser

(57) ABSTRACT

The present invention relates to spinal support and brace devices configured to support the lower back and, more specifically the present invention relates to devices that anchor on portions of the pelvis and are configured to support and/or align one or more Lumbar vertebrae.

24 Claims, 24 Drawing Sheets

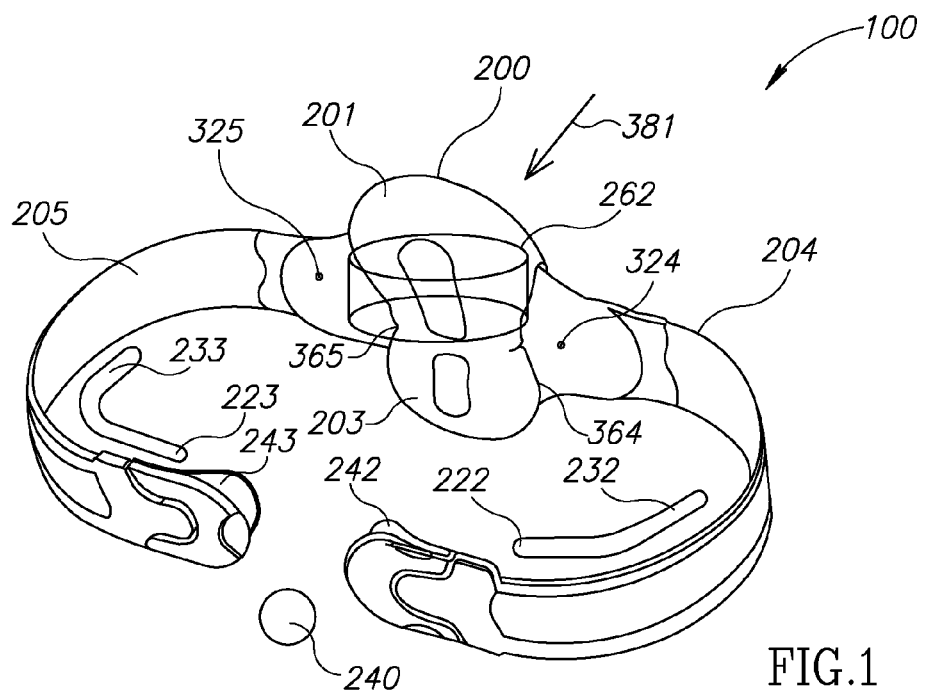
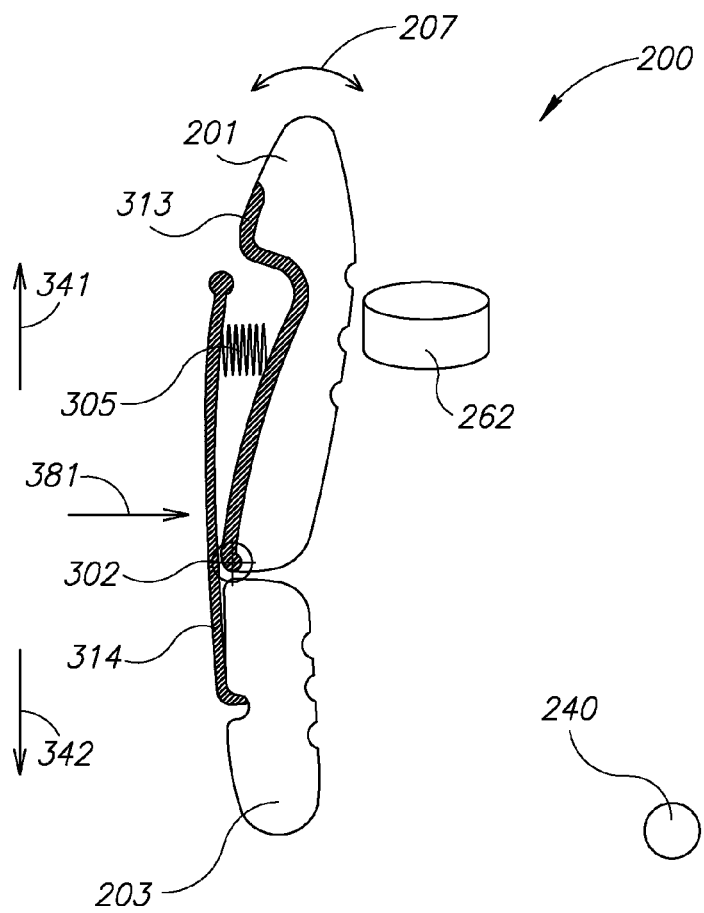

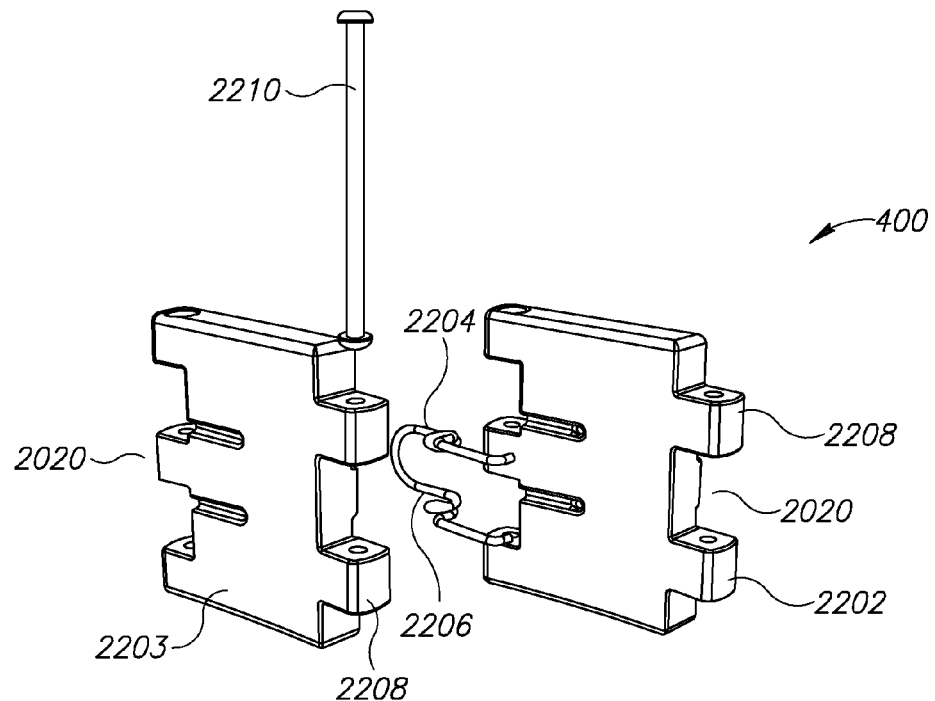
FIG.22
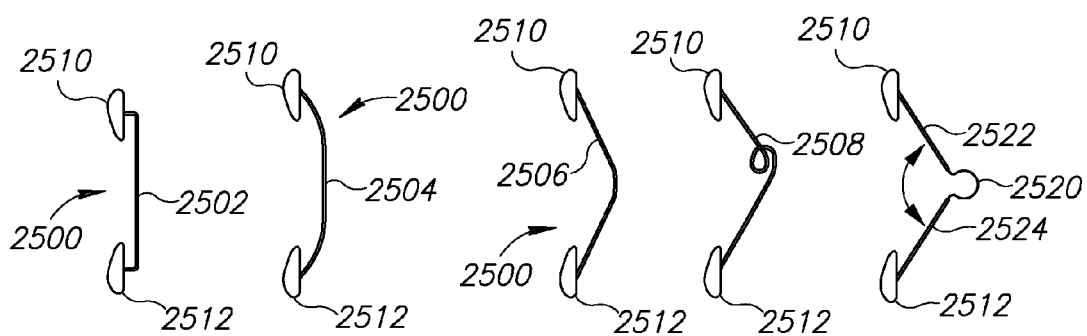
FIG.23A  FIG.23C  FIG.23E
  FIG.23B  FIG.23D

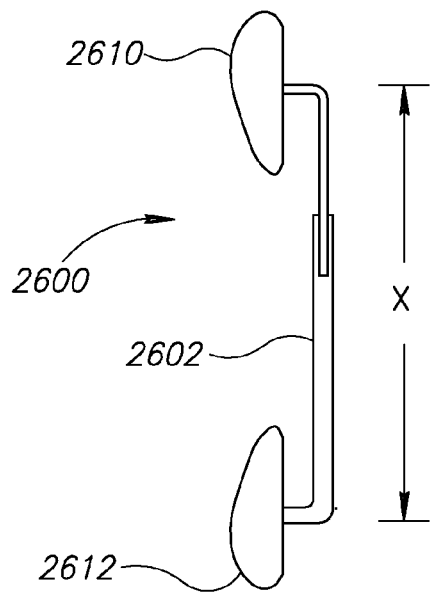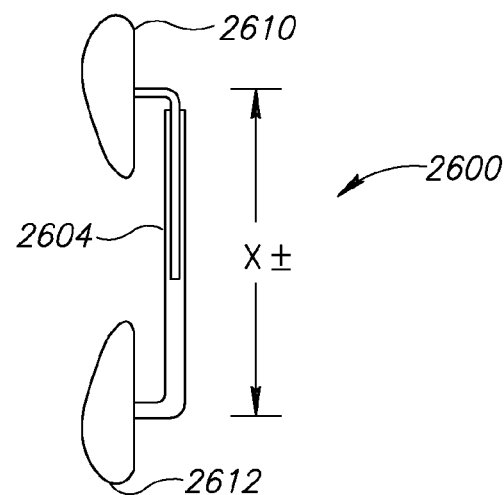
FIG.24A  FIG.24B
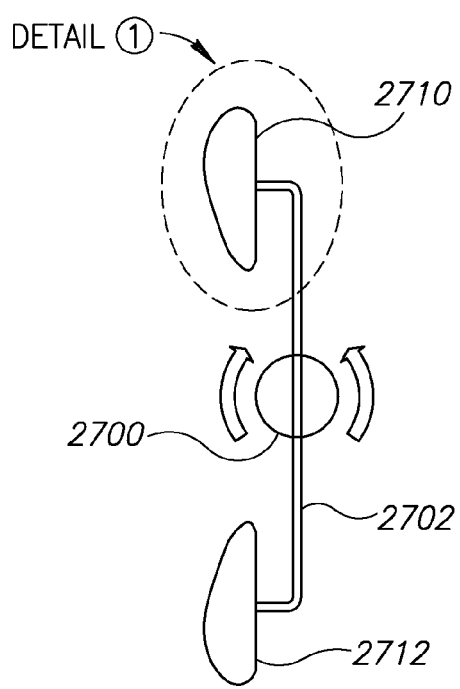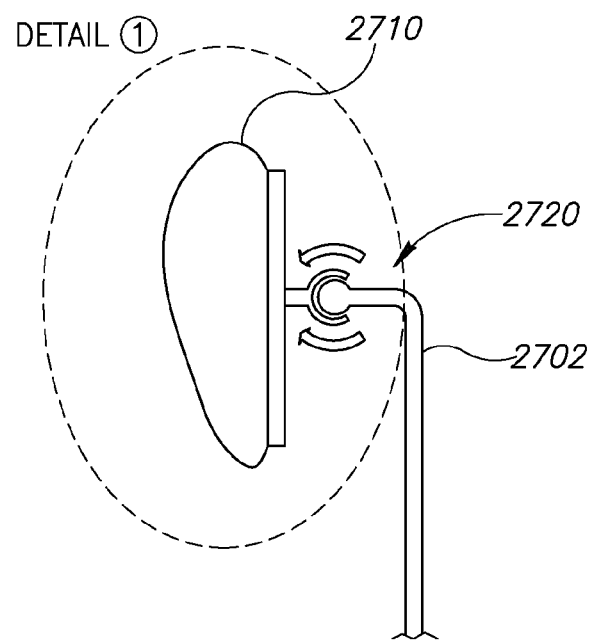
FIG.25A  FIG.25B

PELVIC ANCHOR BRACE AND SPINAL SUPPORT

This application is a continuation in part of PCT Application No. PCT/IL2007/001099 filed on Sep. 5, 2007 which claims priority from U.S. Provisional Application No. 60/842,663, filed on Sep. 7, 2006 and U.S. Provisional Application No. 60/902,047, filed on Feb. 20, 2007; and further claims priority from U.S. Provisional Application No. 61/064,583, filed on Mar. 13, 2008 and U.S. Provisional Application No. 61/136,954, filed on Oct. 16, 2008, all of which are hereby incorporated by reference in its entirety as if fully set forth herein.

FIELD OF THE INVENTION

The present invention relates to spinal support and brace devices configured to support the lower back and, more specifically the present invention relates to devices that anchor on portions of the pelvis and are configured to support and/or align one or more Lumbar vertebrae.

BACKGROUND OF THE INVENTION

Lower back pain is very common in humans and is frequently caused by misalignment between of one or more vertebrae with the pelvis. Current devices aimed at alleviating lower back pain consist of belts that hug the body around the lower back and abdomen therein pulling the back anteriorly toward the abdomen to provide the required support. For example, lower back supports comprising belts that circle the abdomen and press one or more lumbar vertebra anteriorly are known. By pressing the lumbar vertebra anteriorly, the vertebra is encouraged to properly align with the pelvis. By properly aligning the vertebrae with the pelvis, lower back pain is reduced. Examples of lower back supports comprising belts are described in U.S. Pat. No. 5,086,759 to Buddingh, U.S. Pat. No. 7,364,558 to Weaver, U.S. Pat. No. 6,352,074 to Okada and U.S. Pat. No. 5,551,085 to Leighton.

Although these prior art belts provide lower back support they are not amendable to full and active daily use as they reduce mobility of a user. Reduced mobility is prevalent in lower back support belts according to the prior art as they must surround or hug the lower torso; therein fully hugging the lower back and abdominal sections of the user. Fully surrounding the lower torso places undue pressure on the enclosed soft tissue, for example the abdomen. Therefore while aiming to alleviate lower back pain, pressure is exerted on the abdomen which may cause some discomfort. Furthermore, current pelvic belts comprise an abdominal closure reducing comfort over the closure itself, in part leading to the abdominal pressure experienced with such belts.

Additionally current lower back support belts are not automatically or self adjusted to accommodate varying and changing daily activity, therein only providing a single set pressure determined when fitting the belt. Therefore, current support belts do not allow a user to be sufficiently active while wearing the belt. For example, varying activity such as sitting, standing, in transitional stages, walking, picking up a child or playing golf all require varying pelvic postures that are not accommodated for by current lower back support belts as the belt does not adjust itself to provide the appropriate support for the new posture assumed by the user.

SUMMARY OF THE INVENTION

The present invention overcomes these deficiencies of the background art by most preferably providing a pelvic anchor brace comprising a spinal support member that is preferably adjustable to varying postures in accordance with a user's activity, most preferably without transferring or otherwise exerting undue pressure on the surrounding soft tissue such as the abdomen. Most preferably the pelvic anchor brace of the present invention provides a brace that is supported by the bony tissue of the pelvis rather than its surrounding soft tissues.

A preferred embodiment of the present invention provides pelvic anchor brace and a spinal support that is self self-adjusting with the posture and activity of a user most preferably without placing undue pressure on the abdomen rather relying on the rigid tissue for providing the necessary support.

The term pelvic anchor brace within the context of this application refers to a device that may be worn by a user to alleviate lower back pain by providing lumbar support that gains its support from rigid tissue, most preferably from the pelvis. The term pelvic anchor brace may be used interchangeably with the terms lumbar support member, pelvic support brace, pelvic belt, support belt, or the like.

The term cushion may refer to any support structure used to apply a force to a given anatomical region. Most preferably the support structure is provided with padding. The term cushion may be interchangeably referred to throughout the present application as padding, pad, pillow, support structure, pressure element or the like term.

The term pressure element may be referred to throughout the text of the present invention as any element that exerts or applies pressure to a user. A pressure element, for example, is a cushion.

The term attachment element or connection element within the context of the present application may be any element used to link, join, couple, attach or otherwise connect two elements. For example, the joining axis, the pivot point, the upper and lower axis arms are optional forms of attachment elements. Optionally, attachment elements may take the form of clips, loops, connectors or the like.

The term arms within the context of this application refers to flanking members to the right and or left of a central support member. Optionally arms may be provided and may assume a plurality of forms, shapes, and material. For example arms may be provided from optionally shaped materials for example including but not limited to solid structure, wire frame, wire, mesh or the like. Optionally, arms may be fit with a plurality of optional materials and or coverings for example including cloth, silicone, rubber. Optionally, the arms may be provided in a plurality of colors, shapes and sizes that are fashionable.

Optionally the pelvic anchor brace according to the present invention may be optionally provided in an under clothing configuration or similarly as an over clothing configuration, or integrated with clothing.

Optionally the spinal support according to the present invention may be optionally provided in an under clothing configuration or similarly as an over clothing configuration, or integrated with clothing.

Optionally and preferably, the pelvic anchor brace according to preferred embodiments of the present invention anchors about firm tissue structures preferably within the pelvis and most preferably pelvic anchoring is provided with the anterior superior iliac crest, or anterior superior iliac spine also referred to herewith as the ASIS.

A preferable embodiment of the present invention provides a pelvic anchor brace comprising one right arm having an abutment that abuts against an anterior portion of the right pelvic bone, and one left arm having an abutment that abuts against an anterior portion of the left pelvic bone, such that the abutment of the left arm is separated by a distance from the abutment of the right arm.

Optionally, the one right arm and the one left arm each include at least one synchronizing surface configured to synchronize movement between the one right arm and the one left arm.

Optionally the at least one synchronizing surface comprises at least one cog.

Optionally at least one of the one right arm and the one left arm, comprises at least two segments that are rotatably connected.

Optionally the spinal support includes one posterior spinal support that is configured to press against a posterior portion of the spine.

Optionally at least one of: the abutment of: the one right pelvis, and the abutment of the one left pelvis, adjustably extend with respect to the one posterior spinal support.

Optionally at least one of: the one right arm and the one left arm are adjustable to assume at least two angles with respect to the longitudinal axis of the one posterior spinal support.

Optionally the spinal support includes an alignment band that extends between the anterior left arm and the anterior right arm.

Optionally at least a portion of the alignment band comprises an elastic member.

Optionally the alignment band is removably attached to at least one of the left arm, and the right arm.

Optionally the one right arm and the one left arm, comprise at least one resilient arm support.

Optionally the spinal support includes at least two removable arm coverings, comprising at least one first removable covering and at least one second removable covering, wherein the at least two removable arm coverings comprise at least one of:

i) the at least one first removable covering having a first color and the at least one second removable covering having a second color; and ii) the at least one first removable covering having a first compression level and the at least one second removable covering having a second compression level.

According to another aspect of the invention, there is provided a spinal support, comprising one posterior spinal support, comprising one superior padded member configured to press against at least one vertebra, one inferior padded member configured to press below the at least one vertebra, and a curved member attached to the spinal support, the curved member configured to encircle a portion of a pelvis.

In embodiments, the one posterior spinal support is configured to be adjusted to press against the posterior portion of the spine with at least two levels of pressure.

In embodiments, at least one of the one superior padded member, and the one inferior padded member, are positionally adjustable with respect the curved member.

In embodiments, the one posterior spinal support includes a rigid backing, and the one superior padded member is juxtaposed against a compressible member that buttresses against at least a portion of the rigid backing.

In embodiments, a portion of the one superior padded member is rotatably connected to a portion of the one inferior padded member.

In embodiments, a portion of the one superior padded member is resiliently connected to a portion of the one inferior padded member.

According to a further aspect of the invention, there is provided a spinal support, comprising two elongate arms extending substantially anteriorly from one posterior spinal support, comprising one right arm that extends substantially anteriorly around at least a portion of a right pelvic bone, and one left arm that extends substantially anteriorly around at least a portion of a left pelvic bone.

In embodiments, the one left arm has an abutment that abuts against an anterior portion of the left pelvic bone.

In embodiments, the one right arm has an abutment that abuts against an anterior portion of the right pelvic bone.

In embodiments, the one right arm and the one left arm have abutments that abut against anterior portions of the right pelvic bone and left pelvic bone, respectively.

In embodiments, at least one of the abutment of the one right arm, the abutment of the one left arm, adjustably extends with respect to the one posterior spinal support.

In embodiments, at least one of the one right arm, and the one left arm, adjustably extends with respect to the one posterior spinal support.

According to still another aspect of the invention, there is provided a method for manufacturing a spinal support that anchors on a pelvis, comprising making a posterior pad configured to support a portion of the spine, extending a right arm anteriorly from the posterior pad and buttressing a portion of the right arm against an anterior portion of a pelvis, and extending a left arm anteriorly from the posterior pad and buttressing a portion of the left arm against an anterior portion of the pelvis.

In embodiments, the method includes curving the right arm around at least a portion of a right pelvic bone, curving the left arm around at least a portion of a left pelvic bone, and causing the posterior pad to provide a first pressure against the portion of the spine.

In embodiments, the method includes adjusting a curvature of the right arm and the left arm to cause the posterior pad to apply a second pressure against the portion of the spine.

According to still another aspect of the invention, there is provided a method for supporting a portion of a spine, the method comprising providing two curved arms extending from a padded member, pressing an end of a first arm of the two curved arms against an anterior portion of the right pelvis, pressing an end of a second arm of the two curved arms against an anterior portion of the left pelvis, and supporting a portion of the spine with the padded member.

In embodiments, the method includes buttressing the end of the first arm against the anterior portion of the right pelvis, and buttressing the end of the first arm against the anterior portion of the right pelvis.

In embodiments, the method includes adjusting the extension of at least one of the two curved arms with respect to the padded member.

A further preferable embodiment of the present invention provides for a spinal support most preferably providing support to the sacral region and the lordosis of the lumbar spine, preferably comprising at least two or more cushions preferably controllably joined by an axis. Preferably and optionally, the cushions are positioned along the sagittal plane (midline) of the spinal column comprising at least one first (lower) cushion, preferably providing support to the sacral region, and at least one second (upper) cushion, providing support to the lumbar spine. Most preferably, the cushions apply a controllable force to the sacral and lumbar spine therein providing support to the respective regions.

Most preferably the axis joining the cushions is adaptable to the posture of a user, therein providing a user with essentially fluid motion while maintaining contact with the spinal and sacral region to continuously provide support to the respective spinal and sacral regions.

Optionally, at least one upper and at least one lower cushion may be disposed along the spinal process providing both pelvic and spinal support. Optionally and preferably, the cushions are controllably joined along a controllable axis. Optionally, the proximity between an upper and a lower cushion is controllable along the joining axis. Optionally, the joining axis may form a railing along which the cushions are controllably or automatically displaced, for example by motorized or manual methods.

Optionally and most preferably the cushions may be disposed along the joining axis according to the respective pelvic and/or spinal region. Most preferably, the cushions are disposed along the joining axis so as to allow a user kinetic, static and/or any transitional movements therein. For example including but not limited to walking, standing, running, sitting, bending, stretching, jumping, or any transitional movement from one such state to another while maintaining sufficient support integrity to the respective pelvic and spinal region.

Most preferably, the joining axis is made of material providing sufficient support, rigidity, movement, for example including but not limited to plastics, metal, hybrid materials as is known and accepted in the art. Preferably, the joining axis may assume a plurality of shapes in accordance with the anatomy, posture, support basis required by the user. Optionally, the joining axis may assume a shaped for example including but not limited to straight, curved, circular, convex, concave, spring, spring like, acute angel, obtuse angel, the like shape or in any combination thereof. Optionally and preferably, the joining axis may be made of material having varying degrees of elasticity, rigidity, flexibility, pliability or the like in any combination thereof. Optionally, the joining axis may be customized to a user's particular anatomy and/or required support.

Optionally and preferably, the joining axis may further comprise a pivot joint along its axis. Optionally, the pivot may be positioned at a controllable location along the joining axis between the upper and lower cushions defining a corresponding upper and lower arms of the joining axis. Optionally, the pivot location along the joining axis may be determined based on a user's anatomy and/or required support. Optionally and preferably, the pivotal point may provide a free range of motions between the upper and lower arms allowing the positioning of the upper and lower cushions according to the required support. Optionally, the pivotal point provides up to 360 degrees of motion for each plane formed between the upper and lower joining axis arms.

Optionally, the cushions may be controllably coupled to the joining axis using a joint for example including but not limited to a spring joint, static joint, a moveable joint, a manually adjustable joint, a self adjustable joint, a ball and socket joint, a friction joint, a tension joint, a pressure or force based joint, a threaded locking joint, a locking joint, ratchet joint, motorized joint, nut and bolt, telescopic, or the like coupling.

Preferably, the cushions may be disposed along the joining axis at a controllable distance from one another therein defining the distance between the upper and lower cushions. Optionally, the distance separating the upper and lower cushions may be defined by a plurality of methods as is known in the art for example including but not limited to a spring joint, static joint, a moveable joint, an manually adjustable joint, a self adjustable joint, a ball and socket joint, a friction joint, a tension joint, a pressure or force based joint, a threaded locking joint, a locking joint, ratchet joint, motorized joint, nut and bolt, telescopic, or the like coupling.

According to an optional embodiment of the present invention the spinal support comprising at least two cushions joined by a joining axis as described above may optionally and preferably be coupled to a plurality of waistline, abdominal, back or pelvic apparel, devices or support structures for example including but not limited to, arms according to an optional embodiment of the present invention, aprons, robes, clothing, dresses, uniforms, costumes, overalls, belts, motorcyclist wide belt, weight belt, support belt or the like articles that may be worn around the waistline. Optionally, the spinal support may be coupled to a plurality of devices by integrating them with the devices for example a belt, a weight belt or the like pelvic anchor brace as described hereinabove. Optionally, spinal support according to the present invention may be securely and removeably coupled to the waistline apparel. Optionally the secure and removable coupling may be implemented in manners as is known and accepted in the art, for example including but not limited to clips, loops, threaded bolts, wing nuts, nut and bolt, staple, suture, Velcro®, hook and loop, glue or the like couplings as is known and accepted in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a pelvic anchor brace aligned with a schematic view of the pelvis, according to embodiments of the present invention;

FIG. 2 is a side view of a spinal support associated with the pelvic anchor brace of FIG. 1, aligned with a schematic view of a vertebra according to embodiments of the present invention;

FIGS. 18-22 show still another alternative configuration of the pelvic anchor brace shown in FIG. 1, according to embodiments of the present invention.

FIGS. 23A-E show optional embodiments of a spinal support according to a preferred embodiment of the present invention.

FIGS. 24-25 show optional embodiments of a spinal support according to a preferred embodiment of the present invention and optional positioning mechanisms.

DESCRIPTION OF THE PREFERRED EMBODIMENTS

Figure 3:
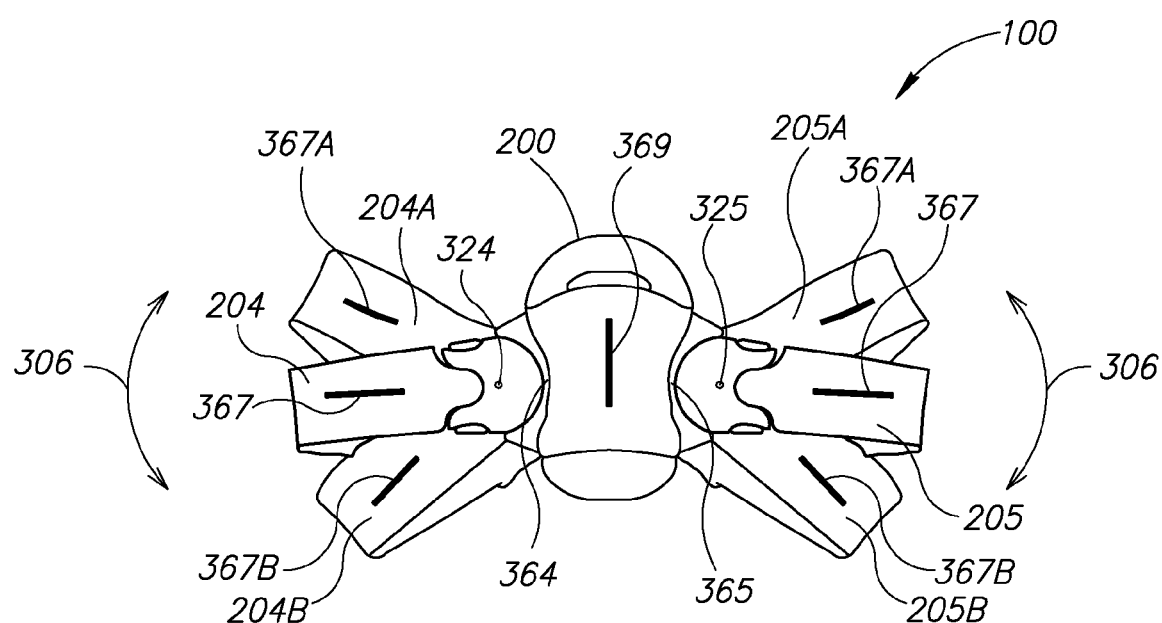
FIG. 3 is a rear view of the pelvic anchor brace of FIG. 1 showing position adjusts of the side arms according to embodiments of the present invention.

The present invention provides a pelvic anchor brace comprising a spinal support member that is preferably adjustable to varying postures in accordance with a user's activity, most preferably without transferring or otherwise exerting undue pressure on the surrounding soft tissue such as the abdomen. Most preferably the pelvic anchor brace of the present invention provides a brace that is supported by the bony tissue of the pelvis rather than its surrounding soft tissues.

A preferred embodiment of the present invention provides pelvic anchor brace and a spinal support that is self self-adjusting with the contour and activity of a user most preferably without placing undue pressure on the abdomen rather relying on the rigid tissue for providing the necessary support.

The principles and operation of a pelvic anchor brace according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 depicts a pelvic anchor brace 100 shown with respect to a lumbar vertebra 262 and a pubic symphysis 240.

Pelvic anchor brace 100 comprises spinal support 200, a right arm 205 and a left arm 204 that extend anteriorly from the spinal support 200. Most preferably, right arm 205 and left arm 204 curve anteriorly to encircle a right pelvis portion 233 and a left pelvis portion 232, respectively. Optionally and preferably the anterior end of arms 204 and 205, defined by abutments 243 and 242 rest on rigid pelvic structure most preferably the right and left anterior superior iliac spine. Preferably and optionally this provides an abdominal section that is free from excess pressure as lumbar support is provided by the counterbalanced with the rigid tissue of the pelvis.

Optionally, the anterior end of right arm 205 comprises a right arm anterior end support member in the form of abutment 243 that is preferably supported against the right anterior pelvic portion 223 and most preferably the right anterior superior iliac spine. Optionally, the anterior end of left arm 204 comprises left arm anterior end support member in the form of abutment 242 that is optionally supported against the left anterior pelvic portion 222 and most preferably the left anterior superior iliac spine Right arm 205 and left arm 204 serve to pull spinal support 200 in an anterior as shown by direction arrow 381 against lumbar vertebra 262, most preferably to provide improved alignment between lumbar vertebra 262 and pelvis portions 232 and 233. Pelvic alignment is further improved with the use of spinal support 200 comprising superior support member 201 and inferior support member 203. Most preferably support members 201 and 203 are provided in the form of a cushion or the like support member.

Optionally and preferably, arms 205 and 204 extend from spinal support 200 and optionally provided with at least one and more preferably a plurality of range of motions for example including the superior/inferior plane, up and down, sideways, out and in, posterior/anterior plane or in any combination thereof or the like. Optionally, the range of motion is provided by at least one or more connectors. For example range of motion in the superior-inferior plane may be provided with a rotational connection for example a pivot as depicted by pivots 324 and 325. Optionally and preferably, pivots 324 and 325 provide arms 204 and 205 with an appropriate range of motion in the superior-inferior plane to allow arms 204 and 205 to conform to the anatomy of a user. The range of motion in the superior-inferior plane preferably provided by pivots 324 and 325 provide for storing, folding or otherwise compacting pelvic anchor brace for example for storage and/or portability.

Optionally, movement within the posterior-anterior plane may be mediated by at least one horizontal swivel connector 365 and/or 364. For example, the corresponding right horizontal swivel 365 and left horizontal swivel 364 preferably provide arms 204 and 205 with an appropriate range of motion in the anterior posterior plane allow arms 204 and 205 to conform to the anatomy of a user. Optionally horizontal swivel 364 and 365 are provided for ease of placing or removing pelvic anchor brace 100 on the user's body. Optionally, horizontal swivel 364 and 365 provide a range of motions from about 0 degrees up to about 360 degrees, optionally up to about 120 degrees.

Most preferably, pelvic anchor brace 100 relieves pain associated with misalignment between lumbar vertebra 262 and pelvis portions 232 and 233 by maintaining the lumbar lordosis, reminding the user about posture and properly positioning the hips.

FIG. 2 shows a side cut-away view of an optional embodiment of spinal support 200 according to the present invention. Preferably spinal support 200 comprises an inferior padded member 203, at least a portion of which is affixed to an inferior backing 314. Spinal support 200 optionally comprises a superior padded member 201, at least a portion of which is affixed to a superior backing 313. Most preferably, inferior backing 314 and superior backing 313 are pivotally and optionally flexibly connected at a connection 302, providing for a range of motion relative to each other. Optionally, pivot 302 may further comprise a resilient member that allows resilient movement of superior padded member 201 in a direction as shown by direction arrow 207. Optionally pivot 302 may be provided in other optional connector or joint forms for example including but not limited to ball and socket or the like to provide additional range of motion for example including sideways, twisiting, front to back or in the directions depicted by arrows 341 and/or 342.

Optionally, pivot 302 may be provided in a plurality of configuration for example including but not limited to a rotatable connection with a compressible buttress 305 between inferior backing 314 and superior backing 313. Buttress 305 preferably acts to press superior padded member 201 toward lumbar vertebra 262 in direction 381.

Optionally, buttress 305 may be provided in a plurality of forms for example including but not limited to silicone rubber, or a balloon, a spring, a pliant curved member, comprises a spring-loaded piston, a pneumatic member, a U shaped pliable member, an S shaped pliable member or the like for supporting superior support member 313 and superior padded member 201 associated therewith.

Optionally superior padded member 201 and/or inferior padded member 203 are provided with a range of motion by assuming the range of motion provided for by backings 313 and 314 respectively. Most preferably, when backing 313 and/or backing 314 are displaced relative to vertebrae 262, as depicted by arrows 381 padded members 201 and/or 203 move with it to apply the appropriate force on the lumbar region. For example, directional arrows 381 depicts displacement forces that may optionally be exerted on backing 313 to encourage superior padded member 201 to place pressure against vertebrae 262 and maintained within a predetermined range by buttress 305.

Optionally, superior padded member 201 and inferior padded member 203 may be associated, dissociated or otherwise repositioned on their respective backings 313 and 314 as shown by arrows 342 and 341. Most preferably associations or disassociation with may be readily achieved with hook and loop type and couplings, buttons, snaps, clips, alligator clips, banana clips, zipper or the like couplings. Most preferably, padded members 201 and 203 may be positioned so as to fit a user most comfortably or exert the desired therapeutic force. Optionally, the location of padded member 201 and 203 may be depicted by a user, practitioner, physician or the like optionally with respect to at least one parameter for example including but not limited to comfort, user anatomy or the like.

Optionally, buttress 305 may comprise a swivel connection therein allowing superior padded member 201 to swivel from side-to-side along a longitudinal axis passing through buttress 305. Similarly, inferior padded member 203 may be connected to backing 314 with a swivel connection allowing side-to-side movement or optionally an angled/rotational movement.

Preferably and optionally, a user may determine the degree of support provided by superior support member 201 and inferior support member 203. Most preferably, a single superior padded member 201 is associated with backing 313 and a single inferior padded member 203 is associated with backing 314. Optionally and preferably a plurality of padded members 201 and or 203 may be respectively associated with backings 313 and 314. Optionally and preferably, the properties and characteristics of padded member 201 and 203 may vary according to at least one and more preferably a plurality of parameters for example including but not limited to shape, dimensions, pressure characteristics, heat characteristics, material, pliability, stiffness, color, smells, textures or the like. Optionally, the parameters may be determined by a user, a practitioner, a physician, or user's anatomy.

Optionally, padded members 201 and 203 may further comprise medicated pads that are optionally incorporated and most preferably controllably associated or disassociated with padded member 201 and/or 203. Optionally, padded members 201 and 203 may be provided with a treatment element for example including but not limited to ultrasound, heat, cold, magnetic, laser, electrical current, TENS, biofeedback, RF, electromagnetic energy, optical or the like treatment element and or forms of energy.

FIG. 3 provides a rear view of pelvic anchor brace 100 showing side arms 204 and 205 pivoting about pivots 324 and 325 in directions 306 showing optional arm positions 204a, 204b, 205a and 205b. Most preferably each arm 204 and 205 is independently pivoted preferably with pivot 324 and 325 providing a range of motion for arms 204 and 205 to assume optional positions about spinal support 200 ranging from 204a to 204b, and 205a to 205b. Optionally, such arm position provides for storing pelvic support brace 100 or for adjusting arms 204 and 205 relative to a user's body as shown in FIG. 4.

Optionally axes 367 longitudinally running through arms 204 and 205 each may assume upward vertical position shown as axes 367A and/or downward vertical positions axes 367B with respect to a longitudinal axis 369 of spinal support 200, for example allowing pelvic anchor brace 100 to become compact for storage in a relatively small space, or optionally for carrying while traveling. Optionally, axes 367 may assume a plurality of optional positions (367A and/or 367B) relative to longitudinal axis 369 that may be formed as a result of combining the range of motion provided by pivot 324 and 325 and by horizontal swivels 364 and 365.

Figure 4:
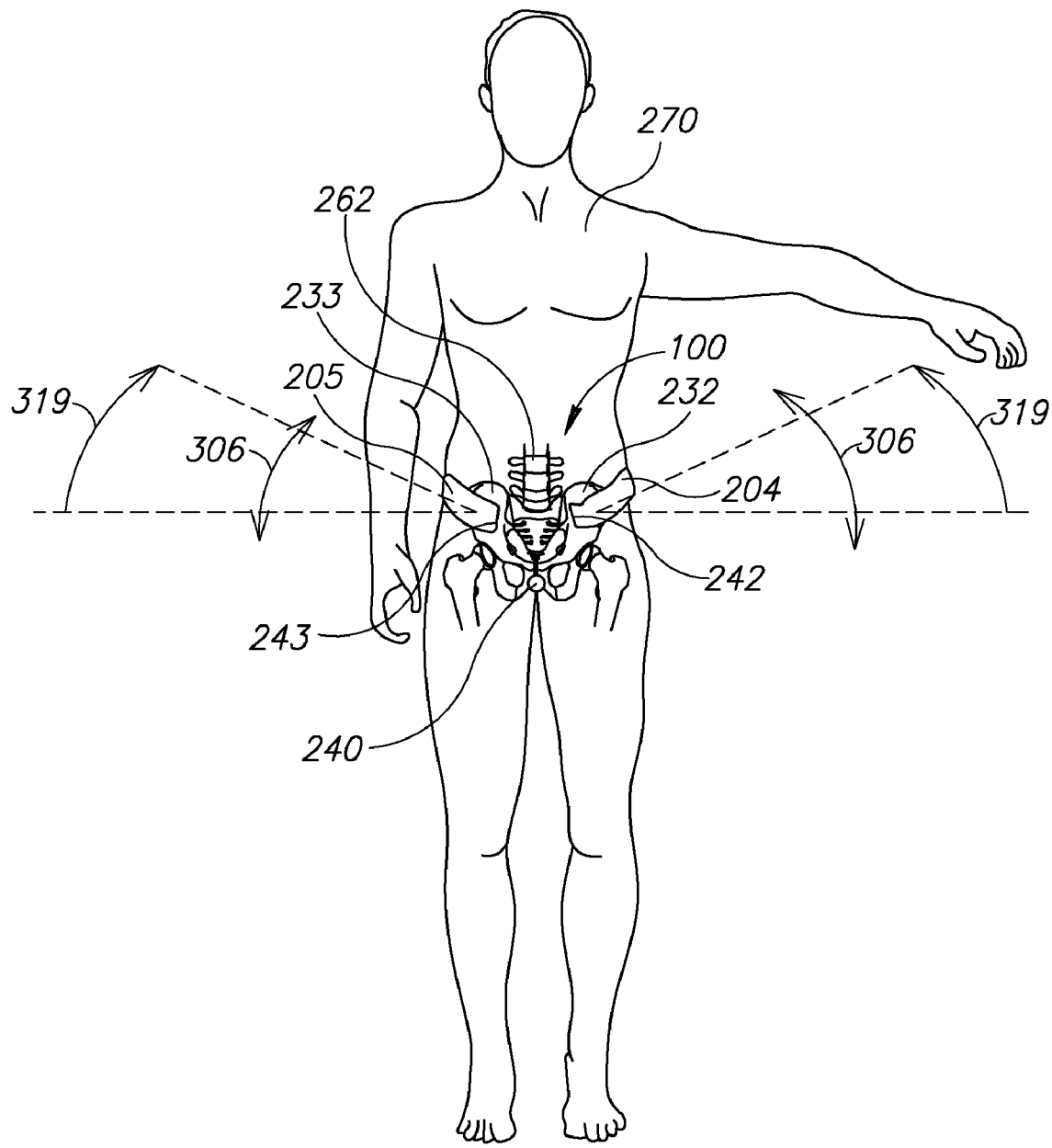
FIG. 4 is a frontal view of the pelvic anchor brace of FIG. 3 on a schematic of a human being, according to embodiments of the present invention.

FIG. 4 provides a frontal view of pelvic anchor brace 100 in use over the pelvis of user 270. Adjustable arms 204 and 205 are shown as they are pivoted in accordance with the anatomy of user 207. Optionally, arms 204 and 205 may be placed so as to fit the pelvic anchor brace 100 on user 207 in a most comfortable position.

Figure 5:
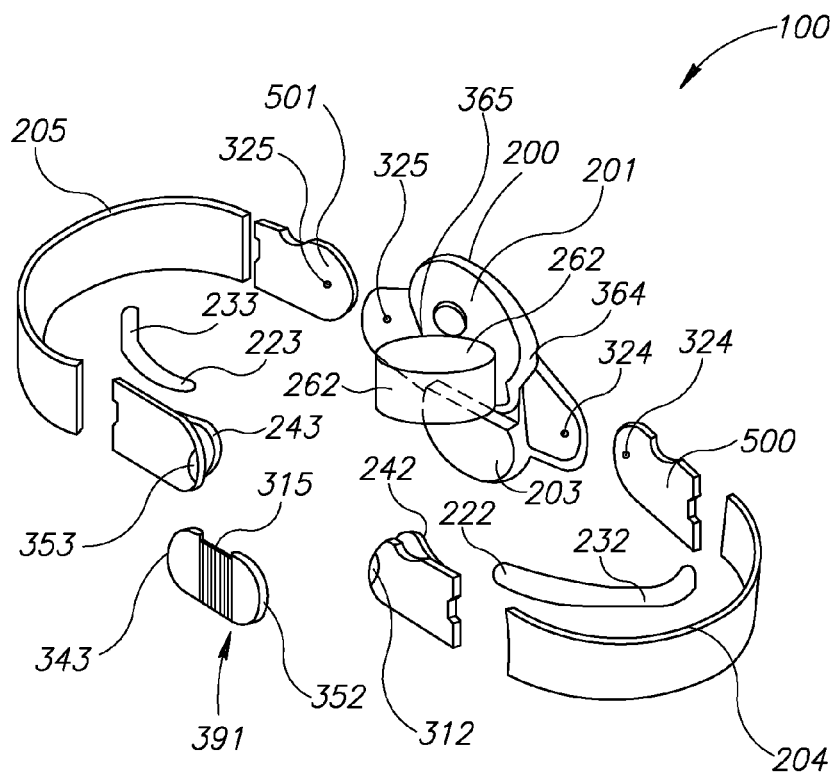
FIG. 5 is an exploded view of the pelvic anchor brace of FIG. 1, according to embodiments of the present invention.

FIG. 5 provides an exploded view of pelvic anchor brace 100 as previously described in FIG. 1, demonstrating that arms 204 and 205 are optionally an preferably realized in modular form. Most preferably, modular portions are particularly adept for personalizing anchor brace 100 to a user's need and or anatomy. For example, the length, shape, tension, materials used to form arms 204 and 205 may be controlled. Optionally, while left arm 204 may be made of a first material having a particular pressure and pliability characteristics while the right arm may be made of different material having alternative properties that are more suited for the right side of the pelvis. For example, the curvature of arms 204 and 205 may be independent of the other. Most preferably, parameters that may be customized to individual arms for example include but is not limited to curvature, length, color, material, resistance, shape, symmetry, tension, pliability, cushion, design, width, or the like parameters.

In this manner, when a user presents for fitting of pelvic anchor brace 100, optionally with by a physician or practitioner, different configurations of arms 204 and 205, that are optionally provided with a kit, may be substituted to ensure user comfort.

FIG. 5 provides a depiction of an optional embodiment of spinal and pelvic brace 100 further comprising an optional alignment band 391 that optionally provides for alignment between left arm 204 and right arm 205 by creating a bridge between left pelvis abutment 242 with right pelvis abutment 243. Alignment band 391 optionally comprises a central portion that is optionally, stretchable, rigid, lockable, flexible, pliable, twistable, springy or the like mediating left tab 352 left connector 312 disposed on left pelvis abutment 242 and a right tab 343 that is preferably amenable to coupling with right connector 353. Optionally, the connection between tabs 352 and 343 and connectors 312 and 353 may be realized with at least one or more variable forms for coupling, for example including but not limited to clips, snaps, buckles, bolts and nuts, hooks and/or hook and loop connectors or the like as is known and accepted in the art. Optionally alignment band 391, inter alia, may be designed and/or colored to provide pleasing aesthetic effects that encourage the user to use pelvic anchor brace 100.

Figure 6:
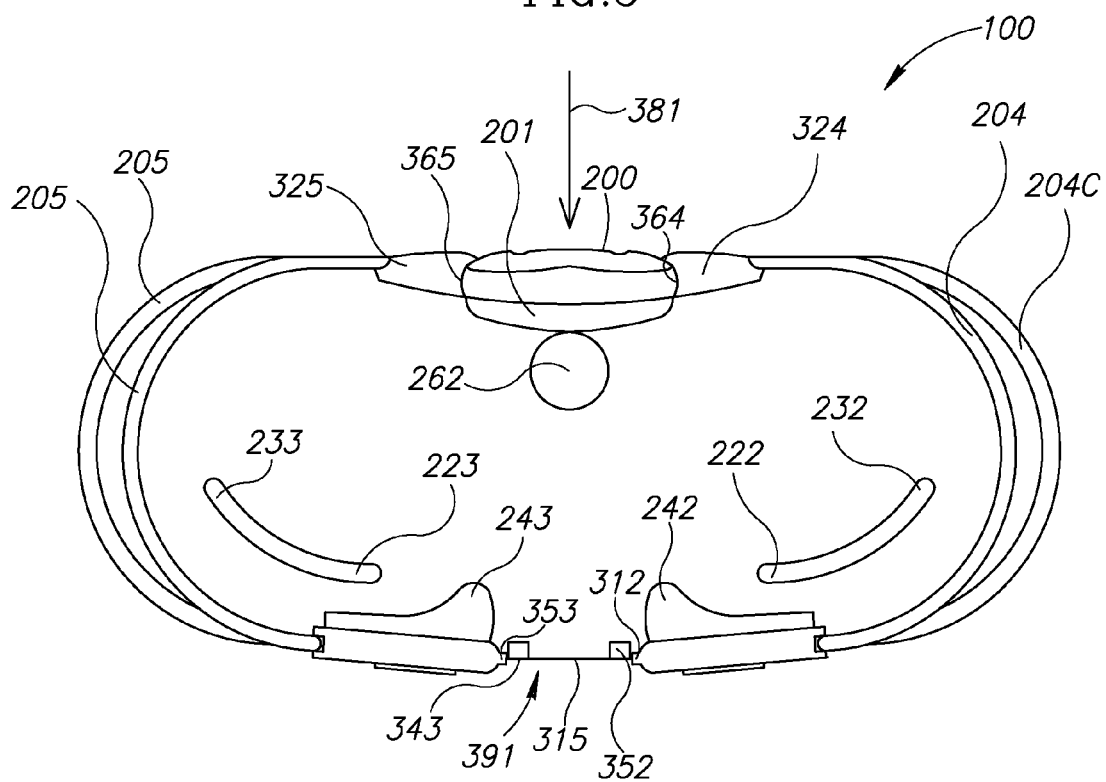
FIG. 6 is an aerial view of the pelvic anchor brace of FIG. 1, according to embodiments of the present invention.

The modular nature of spinal and pelvic brace 100 is further depicted in FIG. 6 wherein arms 204 and 205 may be displaced to arm positions 204C and 205C to better fit a user's anatomy. For example, arms 205C provides a large arching radius to better fit a user having larger inter-pelvic space. Optionally, arms 204 and/or 205 may be changed with other arms to better fit a user. Optionally, the arms may be provided in a plurality of forms for example including links (FIG. 20), segments, overlapping segments, telescopic or the like to provide for control of the arm shape and structure to best suite a plurality of users.

Most preferably, the characteristics of each of abutments 242 and 243, alignment band 391, pivots 324 and 325, arms 204 and 205 may be customized to a user's needs according to at least one or more parameters for example including but not limited to anatomy, posture, user preference, materials or the like parameter.

In still further embodiments, arms 204 and 205 are slidingly attached to pivots 324 and 325 to allow adjustment to the lengths of arms 204 and 205 that extend from spinal support 200.

Figure 7:
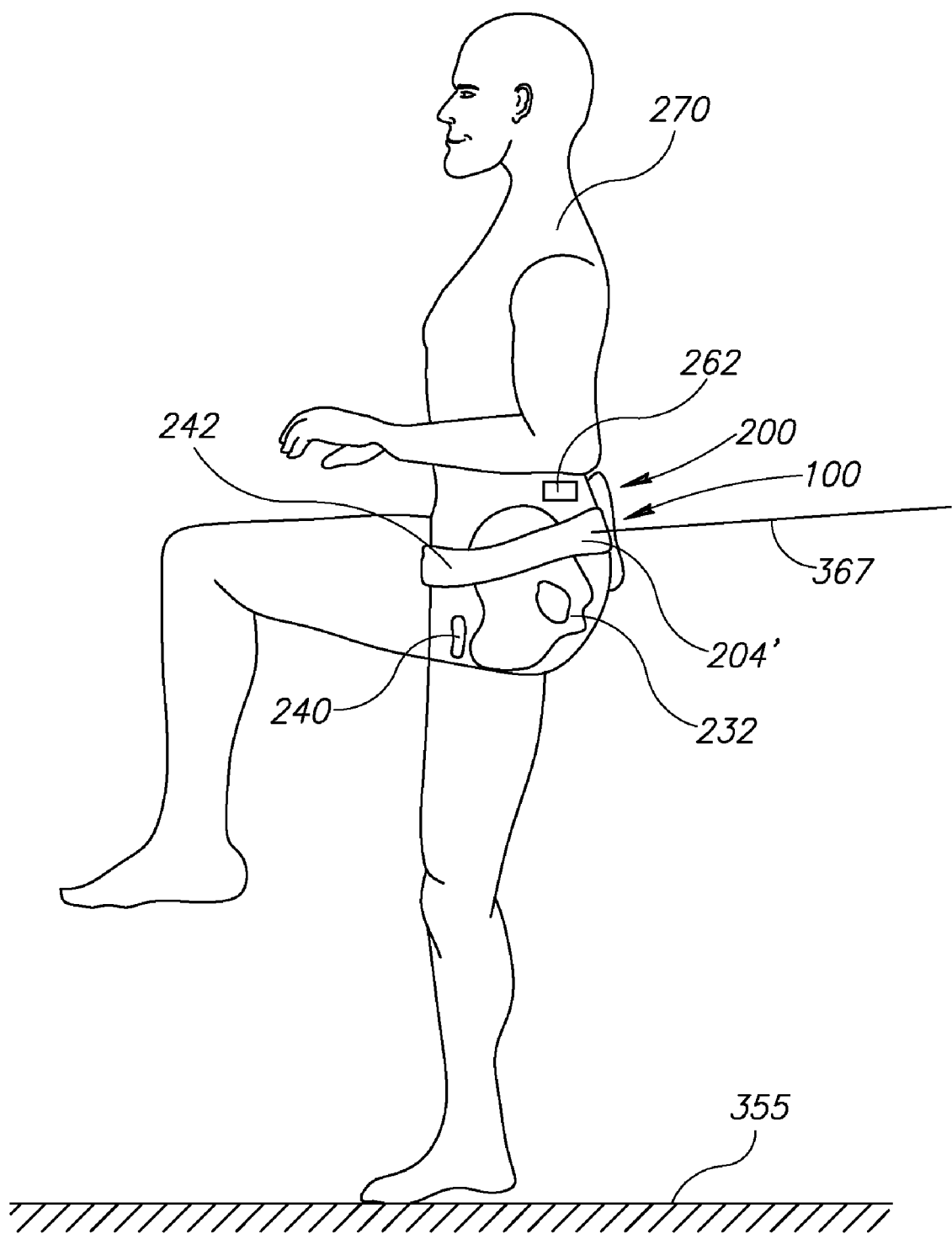
FIG. 7 is a side view of the pelvic anchor brace of FIG. 6 on a schematic of a human being, according to embodiments of the present invention.

FIG. 7 shows a side schematic view of user 270 in which pelvic anchor brace 100 has been equipped with long arc arm 204c having longitudinal axis 367 that is substantially parallel to a support surface 355. Long arc arm 204c, for example, includes a sufficiently long arc to pass directly over right pelvis portion 233 (not shown) without causing irritation to the soft tissue between long arc arm 204c and right pelvis portion 233 (not shown).

Figure 8:
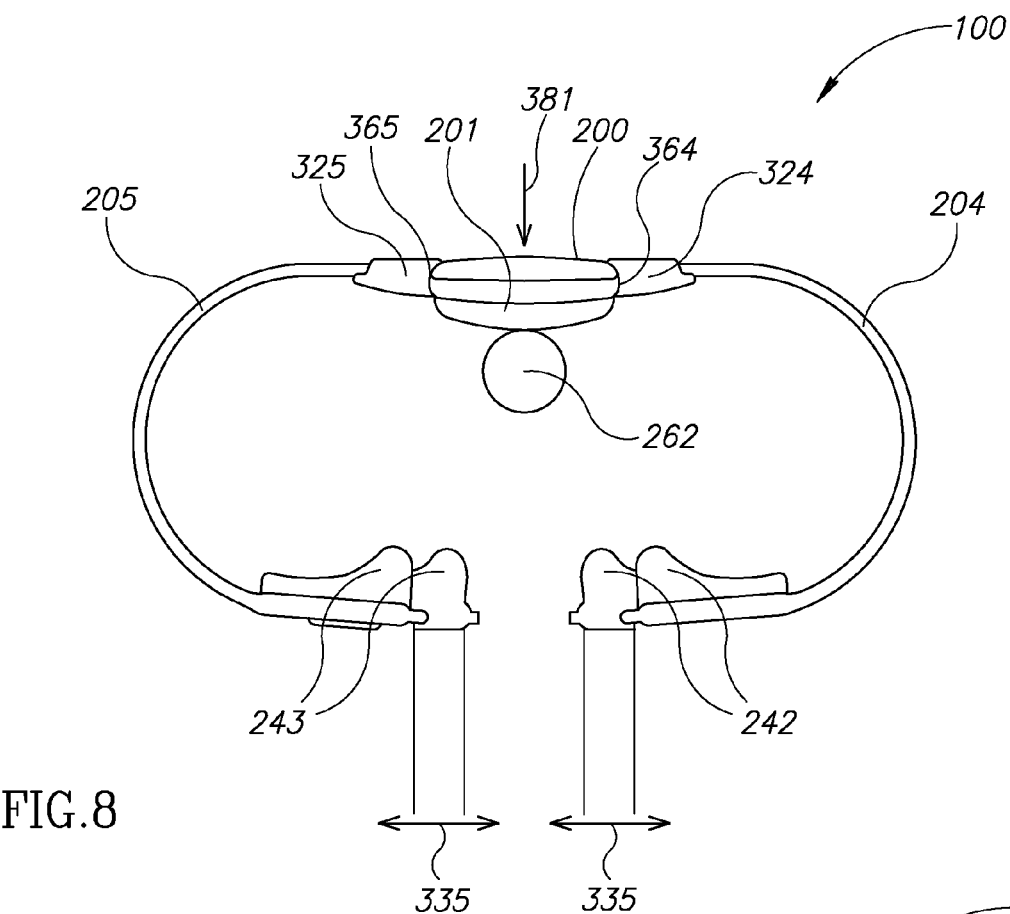
FIGS. 8-9 are aerial views of the pelvic anchor brace of FIG. 1, according to embodiments of the present invention.

FIG. 8 shows further optional adjustability of pelvic anchor brace 100 in which right pelvis abutment 243 and left pelvis abutment 242 adjustably move in adjustment directions 335 with respect to arms 204 and 205 respectively.

In additional embodiments, right arm 205 and left arm 204 are shown moving in and out in directions 335 with respect to pivots 324 and 325, respectively, thereby changing the extension distance of arms 204 and 205 with respect to spinal support 200.

Figure 9:
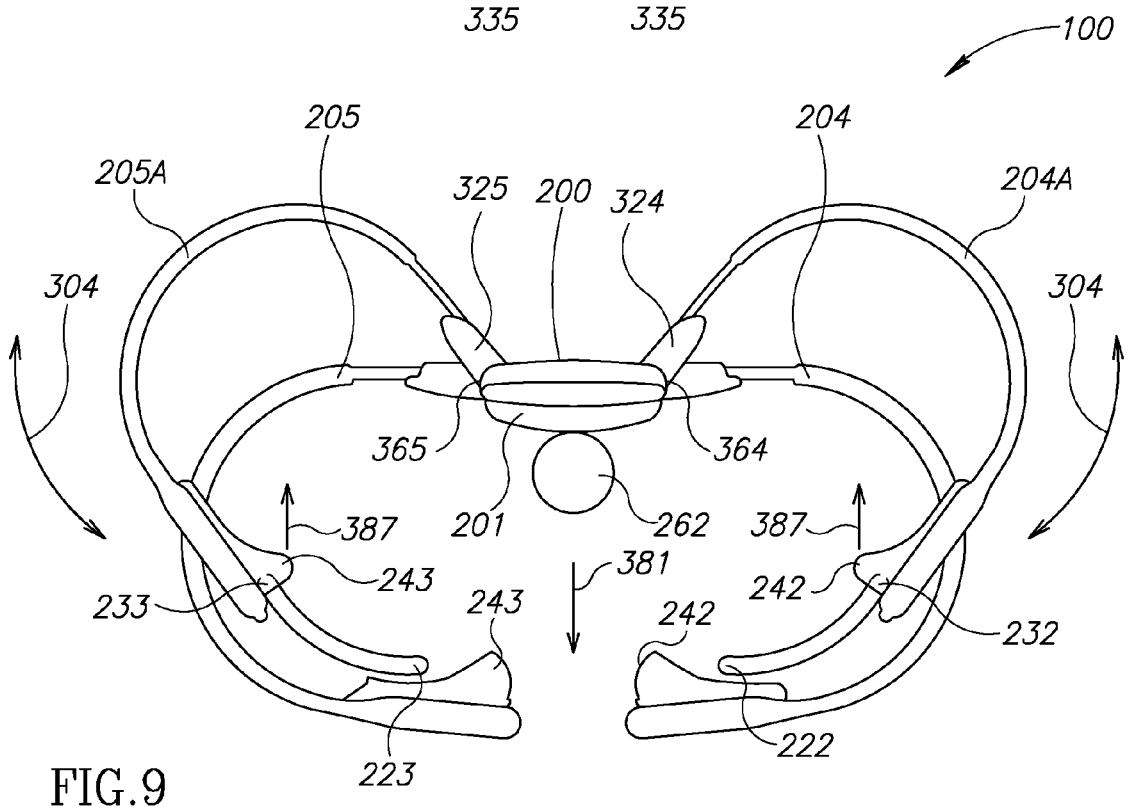

FIG. 9 shows an embodiment in which right arm 205 swivels in directions 304 preferably about right horizontal swivel 365, while left arm 204 swivels in directions 304 preferably about left horizontal swivel 364, most preferably allowing a user to quickly and easily place brace 100 into its position, and most preferably into its most comfortable position.

Optionally right horizontal swivel 365 and left horizontal swivel 364 can be fixed in a specific position with respect to spinal support 200. In this manner arms 204 and 205 bring pelvis abutments 242 and 243 in a posterior direction 387 against anterior pelvis portions 222 and 223, thereby causing spinal support 200 to move in anterior direction 381 against vertebra 262, affording greater alignment-causing pressure against vertebra 262.

Optionally, right horizontal swivel 365 and left horizontal swivel 364 allow arms 204 and 205 to swing backward so the user easily puts spinal support 200 in position and then swing arms 204 and 205 forward. In this manner, spinal pelvic brace 100 allows the user to easily install pelvic anchor brace 100. Additionally, arms 204 and 205 may optionally swing backward to allow easy and/or quick removal.

Optionally arms 204 and 205 comprise resilient material and may be adjusted, for example by bending, to bring anterior pelvic abutments 242 and 243 closer to spinal support 200.

Figure 10A:
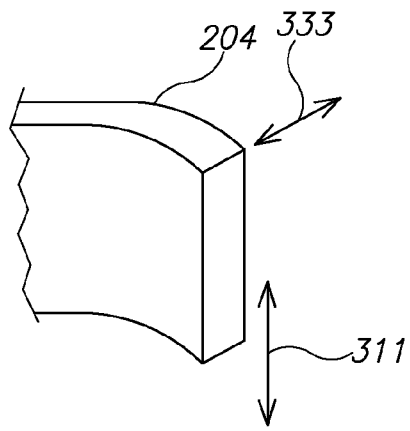
FIGS. 10A-10C are cross sectional views of the arms of the pelvic anchor brace of FIG. 1, according to embodiments of the present invention.
Figure 10B:
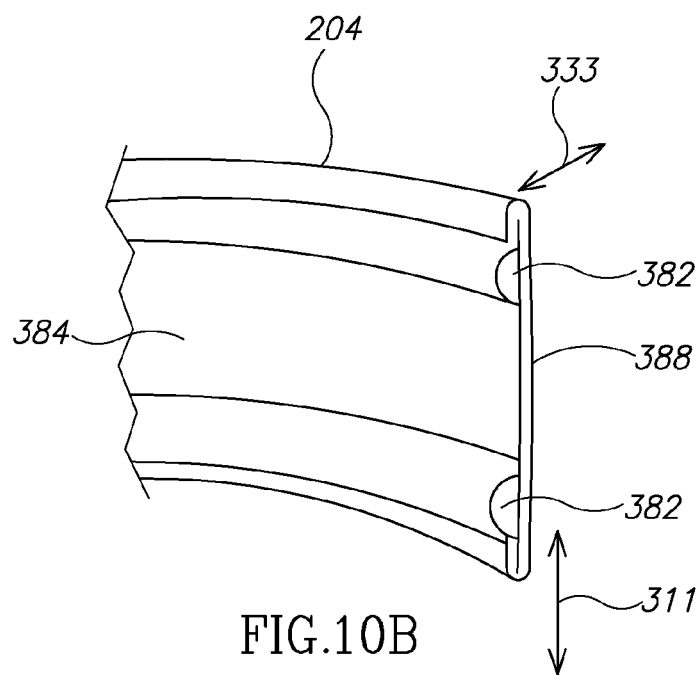
Figure 10C:
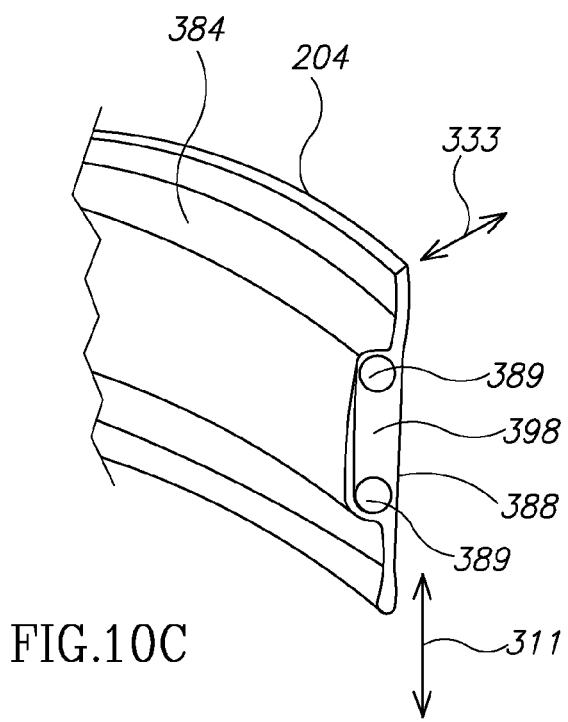

FIGS. 10A-10C show a variety of configurations of arm 204. FIG. 10A shows arm 204 comprising a substantially rectangular cross section of a resilient material.

FIG. 10B shows arm 204 comprising a forward face 388 and a rearward face 384 in which rearward face 384 substantially follows the contour of resilient arm supports 382.

Optionally, the forward face 388 and/or the rearward face 384 are removably connected to the resilient arm supports 382.

Optionally, multiple removably connected forward faces 388 and/or rearward faces 384 in a variety of colors and/or designs that are optionally provided in a kit so that a user may exchange a forward faces 388 having a first color with a forward face 388 having a second color. In this manner, when pelvic anchor brace 100 is worn exterior to the user garments, the user has the option to configure pelvic anchor brace 100 to match the colors of a variety of garments.

In still further embodiments, multiple removably connected forward face 388 and/or rearward face 384 comprise compressible materials, each having a different compressibility. By switching between the various forward faces 388 and/or rearward faces 384, the user changes the pressure with which pelvic anchor brace 100 presses on pelvic abutments 242 and 243, thereby influencing the comfort level provided by arms 204 and 205.

Optionally, resilient arm supports 382 have a substantially semicircular cross sectional shape.

In FIG. 10C, rearward face 384 includes a recess 398 between resilient arm supports 389, optionally this further defines a recess between at least a portion of rearward face 384 and at least a portion of forward face 388.

While resilient arm supports 389 are shown as having substantially circular cross section, arm supports 389 can have any one of a variety of cross sectional configurations, including: triangular, rectangular or any one of many geometrical shapes.

Optionally, resilient arm supports 382 (FIG. 10B) and 389 (FIG. 10C), and arms 204 and 205 (FIG. 9) comprise materials selected from the group consisting of nitinol, stainless steel shape memory materials, metals, synthetic biostable polymer, a natural polymer, titanium, pyrolytic carbon, carbon-reinforced materials and plastic or the like as is known and accepted in the art.

Optionally, any of the embodiments shown may be provided to comprise a silicone rubber (for example, Silastic by Dow-Corning Corporation, Midlan, Mich., U.S.A.), a thermoset material, or a polyester (ester imide), (for example Dacron® by Invista, Wichita, Kans., U.S.A.) and/or combinations thereof. Alternatively, superior padded member 201, inferior padded member 203, left pelvis abutment 242 and/or right pelvis abutment 243, optionally comprise sponge, foam materials and any one of a variety of compressible materials.

Figure 11:
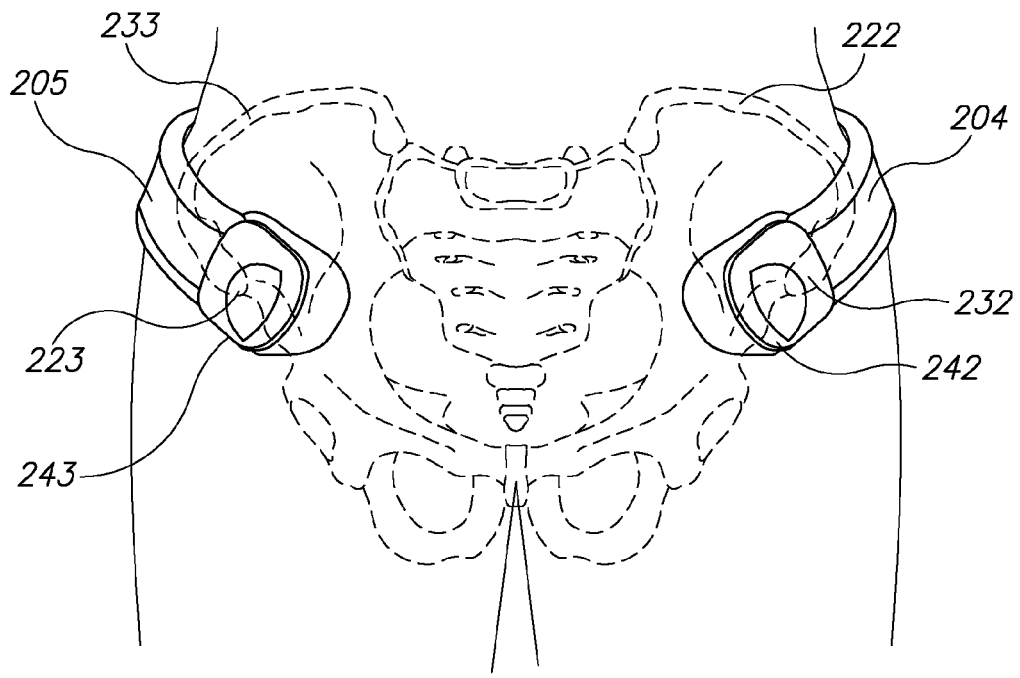
FIGS. 11-13 are representative pictures of the pelvic anchor brace shown in FIGS. 1-2 as worn by a user, according to embodiments of the present invention.
Figure 12:
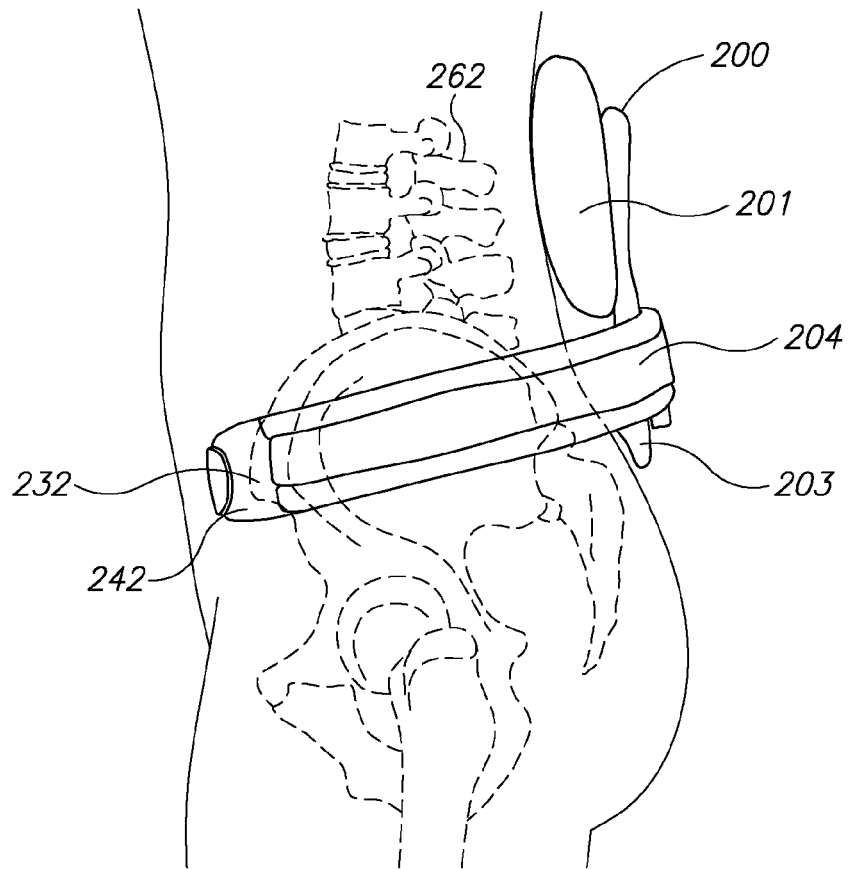
Figure 13:
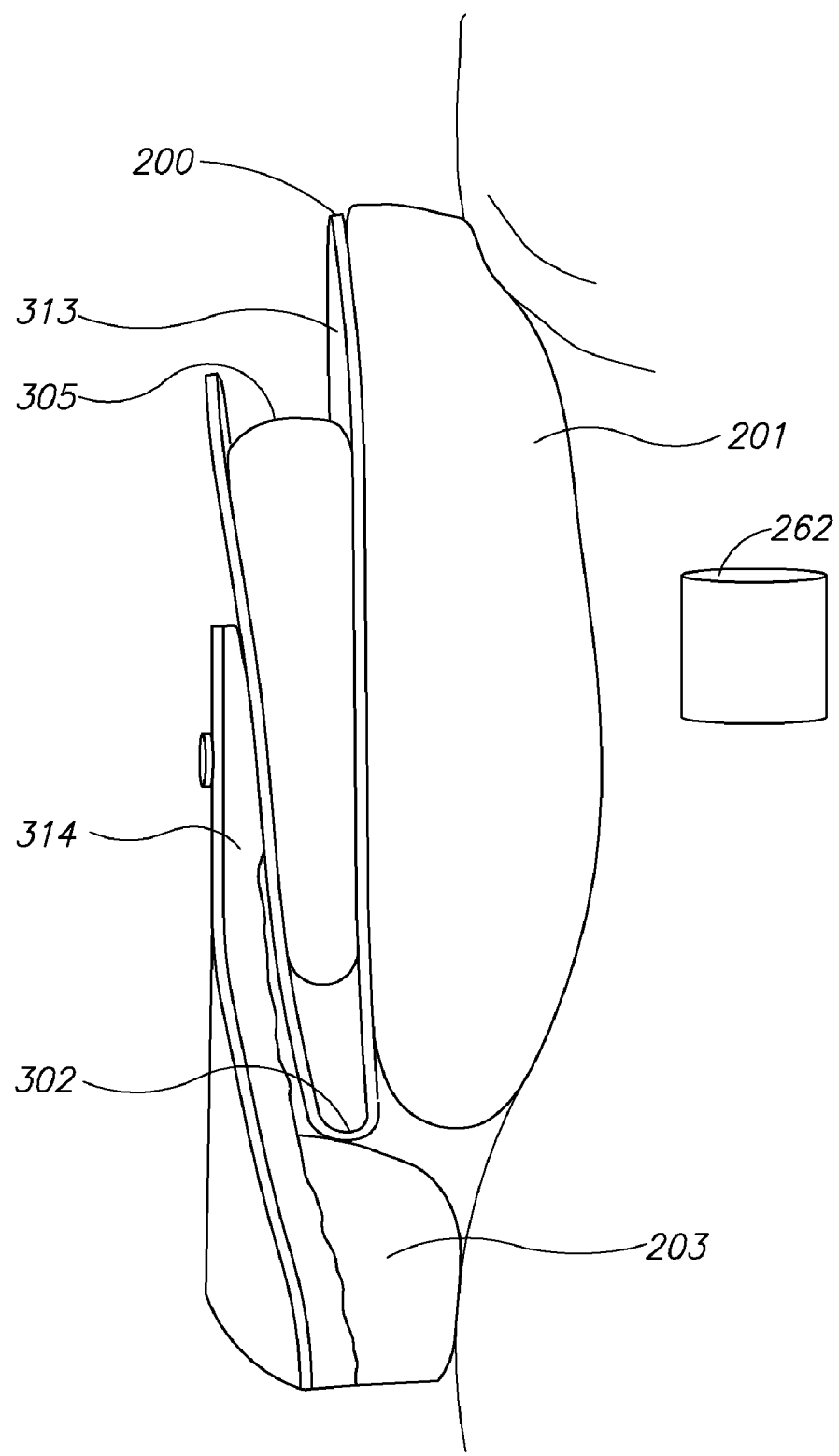

FIGS. 11-13 provide alternate perspective views of the pelvic and spinal brace in representative pictures of the pelvic anchor brace as described earlier and worn by a user, according to embodiments of the present invention;

FIG. 13 provides a side view of an optional embodiment of spinal support 200 as described in detail in FIG. 2, where similar numbering is used to identify similarly functioning parts. FIG. 13 shows spinal support 200 comprising an optional pivot 302 that is realized in the form of an integral joint providing a "U" shaped superior backing. Superior backing 313 comprises an anterior segment for coupling to superior padded member 201 providing lumbar support for user 207; a posterior segment for associating with inferior backing 314, wherein optionally and preferably the posterior and anterior segments are mediated by flexible integral joint 302 providing flexibility. Most preferably buttress 305 rests between the posterior and anterior segments of backing 313 within the recess formed by integral joint 302.

FIGS. 14-19 show views of other embodiments of a pelvic anchor brace according to the present invention, demonstrating various adjustable components for securely and comfortably placing the brace on the user while accommodating movements of the user. It should be noted that these drawings focus upon the mechanical aspects of the brace, such that the complete product may optionally have one or more additional features or components that are not shown, such as covering, padding or cushioning for example.

Figure 14:
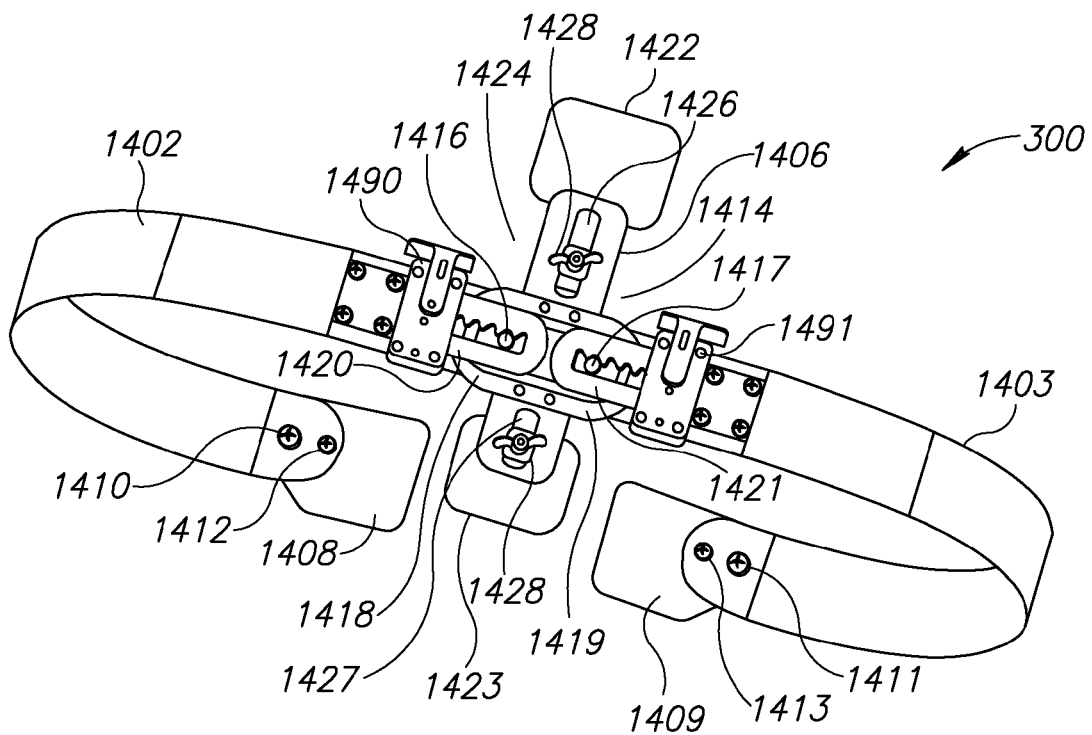
FIGS. 14-17 show an alternative configuration of the pelvic anchor brace shown in FIG. 1, according to embodiments of the present invention.
Figure 15:
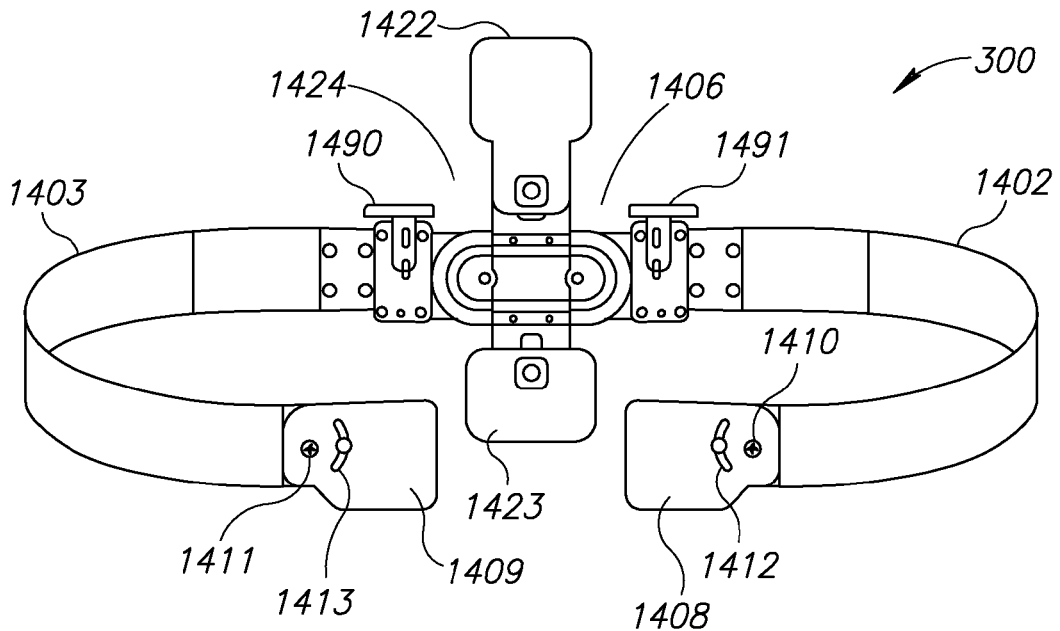

As shown in FIG. 14, an embodiment of a pelvic anchor brace 300 according to the present invention features a left arm 1402 and a right arm 1403, connected to a spinal support 1406 and which curve anteriorly from spinal support 1406 with respect to the body of the user (not shown). Left arm 1402 and right arm 1403 each feature a left and right pelvic abutment 1408 and 1409, respectively. Each of left and right pelvic abutment 1408 and 1409 is supported by the left or right pelvic areas, at the anterior superior iliac spine-ASIS of the user, respectively (not shown). It should be noted that by "pelvic area" it is meant any location in the vicinity or proximate location to the pelvic bones at the front of the body, known as the anterior superior iliac spine-ASIS.

Optionally and preferably, in order to better adjust the position of each of left and right pelvic abutment 1408 and 1409, left and right pelvic abutment 1408 and 1409 are each adjustably joined to left arm 1402 and right arm 1403, more preferably through a left pivot 1410 or a right pivot 1411 as shown. Also optionally and more preferably, a left locking mechanism 1412 and a right locking mechanism 1413 respectively lock the position of each of left and right pelvic abutment 1408 and 1409, respectively. As shown with respect to FIG. 15 (which shows pelvic anchor brace 300 in a frontal view), left and right locking mechanisms 1412 and 1413 may each optionally comprise a screw or other tightening or locking device.

Turning back to FIG. 14, arms 1402 and 1403 are preferably joined to spinal support 1406 through an adjusting mechanism 1414, which enables arms 1402 and 1403 to move in a synchronized manner, thereby ensuring symmetrical positioning on the body.

Figure 17:
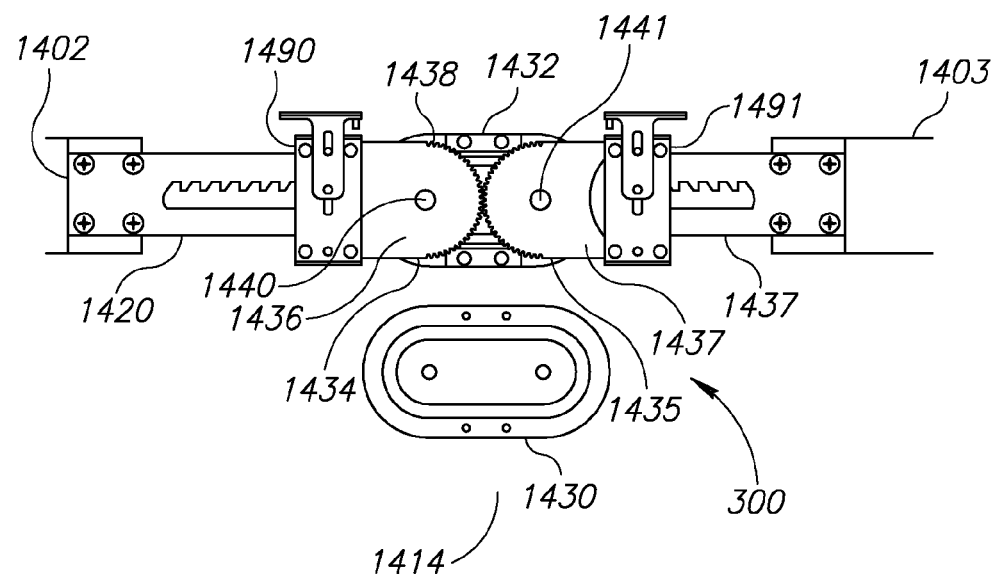

Adjusting mechanism 1414 preferably enables both continuous synchronized pivotable movements, as described in greater detail with regard to FIG. 17, and also horizontal movements which may optionally be limited to one of a plurality of fixed positions. With regard to the latter type of movement, adjusting mechanism 1414 preferably comprises a plurality of pegs, shown as a left peg 1416 and a right peg 1417, each of which is attached to spinal support 1406, preferably through left and right extensions 1418 and 1419, respectively. Left and right extensions 1418 and 1419 preferably project horizontally or substantially horizontally from spinal support 1406. A plurality of teeth on each of a left and a right ratchet 1420 and 1421, respectively, engage with left and right pegs 1416 and 1417, respectively, permitting horizontal movement to one of a plurality of fixed positions. Left and right ratchets 1420 and 1421 may optionally and preferably be locked with left and right locking mechanisms 1490 and 1491, respectively, so as to prevent such movement and hence to fix the horizontal location of left and right ratchets 1420 and 1421. Upon depressing left and right locking mechanisms 1490 and 1491, left and right ratchets 1420 and 1421 may optionally be moved to permit adjustment of arms 1402 and 1403.

According to some embodiments of pelvic anchor brace 300, spinal support 1406 comprises a superior support 1422 and an inferior support 1423, connected through a connector 1424 as shown. Connector 1424 preferably features a superior slot 1426 and an inferior slot 1427 for slidably engaging superior support 1422 and inferior support 1423, respectively. Each of superior support 1422 and inferior support 1423 may optionally be locked in a fixed position within slots 1426 and 1427, respectively, by a screw 1428 as shown.

In place of or in addition to connector 1424, optionally superior support 1422 and inferior support 1423 may optionally be connected to one of a plurality of different approximately parallel arms on each side of the user (not shown). Also each of superior support 1422 and inferior support 1423 (and/or their respective padding or cushioning, not shown) may optionally comprise one or more of magnets, heated pads, vibration devices, pillows and the like (not shown); also each of superior support 1422 and inferior support 1423, as well as the frontal buttressing (for example any portion of arms 1402 and 1403) may optionally have cushions or padding to interface and fit more comfortably with the body (not shown). These cushions or padding may optionally have different shapes and be attached in a variety of ways. The shape and size of the cushions, especially superior support 1422, are important for comfort and also for the therapeutic effect—the thicker the cushion, the more pressure it exerts on the spine. This is in addition to the springy effect of the spinal support connecting the upper and lower cushions (not shown).

Figure 16:
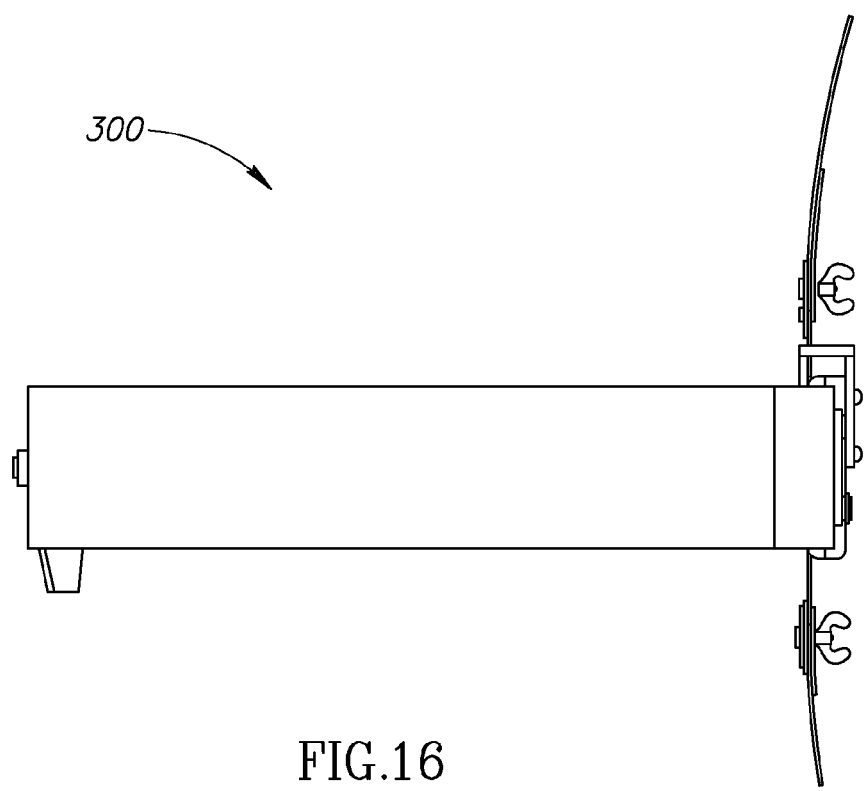

FIG. 16 shows a side view of the brace as seen from the left side.

FIG. 17 shows adjusting mechanism 1414 as viewed from the rear, in which a covering plate 1430 has been removed and in which arms 1402 and 1403 are fully extended horizontally. Adjusting mechanism 1414 as shown preferably comprises a cogging mechanism 1432, which comprises left and right sets of a plurality of engagable teeth 1434 and 1435, respectively. Sets of teeth 1434 and 1435 are each preferably disposed along an edge of left and right curved portions 1436 and 1437, respectively. Left and right curved portions 1436 and 1437 are preferably also connected to a back plate 1438 with left and right pivots 1440 and 1441, respectively, such that left and right curved portions 1436 and 1437 engage in each in a pivotable, cogged manner. The synchronization of movement between the arms 1402 and 1403 may optionally be achieved also through other ways besides cog wheels, such as through friction, having a belt connecting both sides, etc.

As for pelvic anchor brace 100 described above, pelvic anchor brace 300 optionally includes a cover (not shown), such as a silicone over-mold which can be shaped, and colored aesthetically.

Arms 1402 and 1403 of pelvic anchor brace 300 optionally comprise a springy material, for example a metal, which can embrace the user with gentle pressure and/or be adjusted in curvature to properly fit the user; arms 1402 and 1403 may optionally comprise any material or combination thereof as described with regard to other embodiments of the pelvic anchor brace according to the present invention.

FIGS. 18-22 show views of different aspects of some embodiments of an exemplary pelvic anchor brace in which the arms comprise a combination of links and springs.

Figure 18:
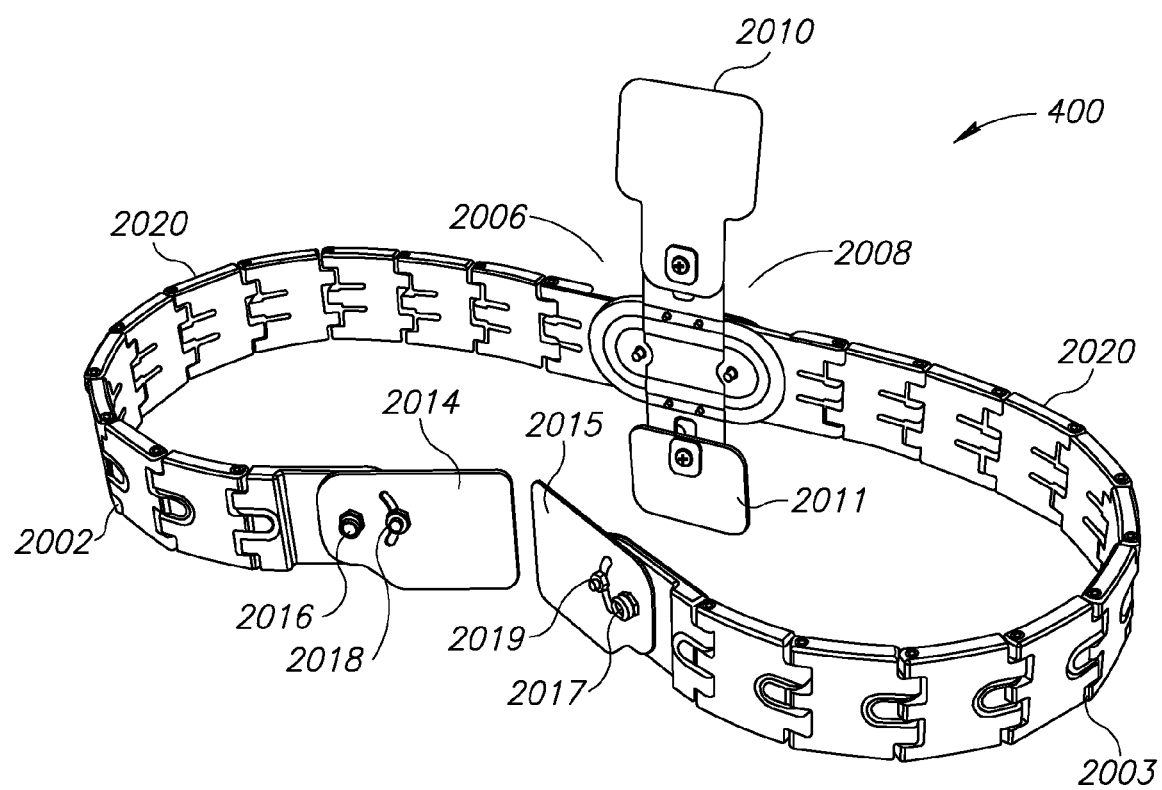

FIG. 18 shows a frontal view of a pelvic anchor brace 400, which preferably comprises a left arm 2002 and a right arm 2003 connected to a spinal support 2006 through a synchronizing mechanism 2008, which enables arms 2002 and 2003 to move in a synchronized manner, thereby ensuring symmetrical positioning on the body. Synchronizing mechanism 2008 may optionally be implemented as for the embodiments of FIGS. 14-19, for example. Spinal support 2006 may also optionally comprise a superior support 2010 and an inferior support 2011, connected through a connector 2012 as shown, which may optionally be implemented as for the embodiments of FIGS. 14-17, for example.

Left and right arms 2002 and 2003 may optionally each comprise left and right pelvic abutments 2014 and 2015 as shown. Optionally and preferably, in order to better adjust the position of each pelvic abutment 2014 and 2015, left and right abutment 2014 and 2015 are each adjustably joined to left arm 2002 and right arm 2003, more preferably through a left pivot 2016 or a right pivot 2017 as shown. Also optionally and more preferably, a left locking mechanism 2018 and a right locking mechanism 2019 respectively lock the position of each of left and right pelvic abutment 2014 and 2015, respectively. All of these components may optionally be implemented as for the embodiments of FIGS. 14-17, for example.

Each of left and right arms 2002 and 2003 preferably comprise a plurality of linked segments 2020 as shown. Optionally however, each of left and right arms 2002 and 2003 comprises such linked segments 2020 in combination with one or more portions that do not have such linked segments 2020 (not shown).

Each segment 2020 can optionally be of different shapes, for example square, round, oval or hexagonal. Alternatively, all segments 2020 of a given pelvic anchor brace 400 may optionally have a specific shape, such as square, round, oval or hexagonal.

Each linked segment 2020 is preferably connected to at least one other linked segment 2020 through a flexible connection (not shown; see FIGS. 20-22 for example), such that each linked segment 2020 is able to move flexibly with regard to the other linked segment(s) 2020 to which linked segment 2020 is connected. Such flexible movement may optionally and preferably comprise pivotable and/or torsional and/or sliding movement. Preferably the flexible movement is possible within a fixed range.

Optionally, linked segment 2020 adjacent to synchronizing mechanism 2008 can be of different lengths or changeable/adjustable length to permit horizontal movement and hence adjustability of arms 2002 and 2003, for example replacing the ratchet mechanism of the previous embodiment, and hence enabling the size (length) of arms 2002 and 2003 to be changed to fit different individuals.

Figure 19:
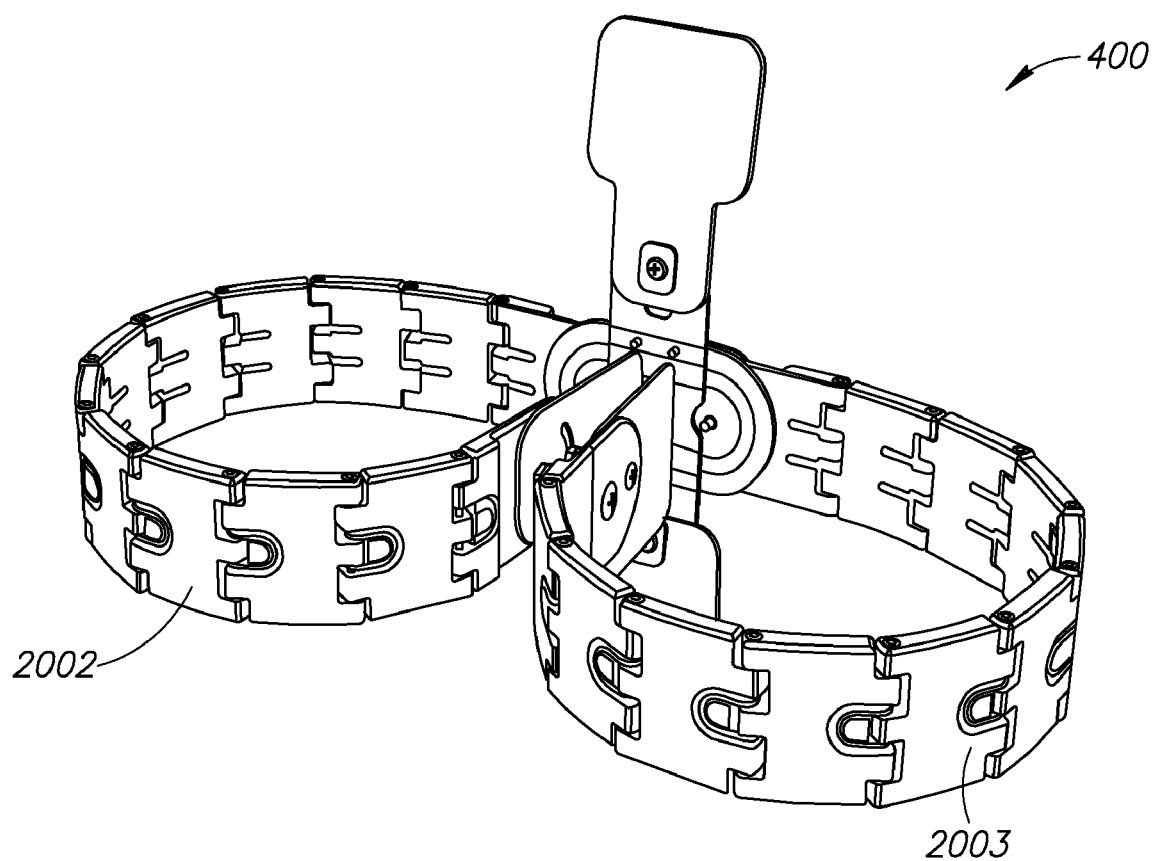

FIG. 19 shows pelvic anchor brace 400 of FIG. 18 in which arms 2002 and 2003 are folded inwardly to reduce space requirements during storage.

Figure 20:
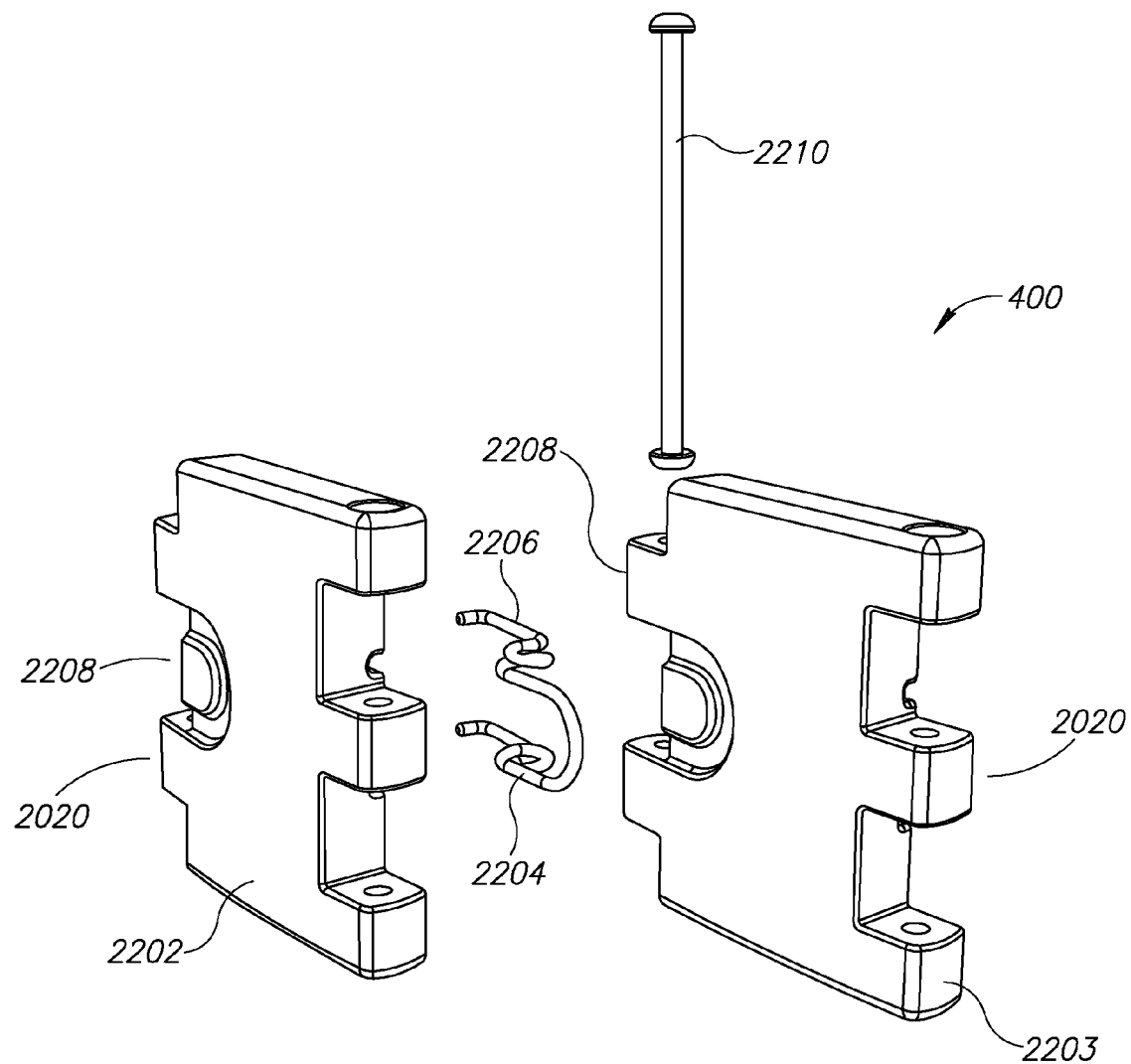
Figure 21:
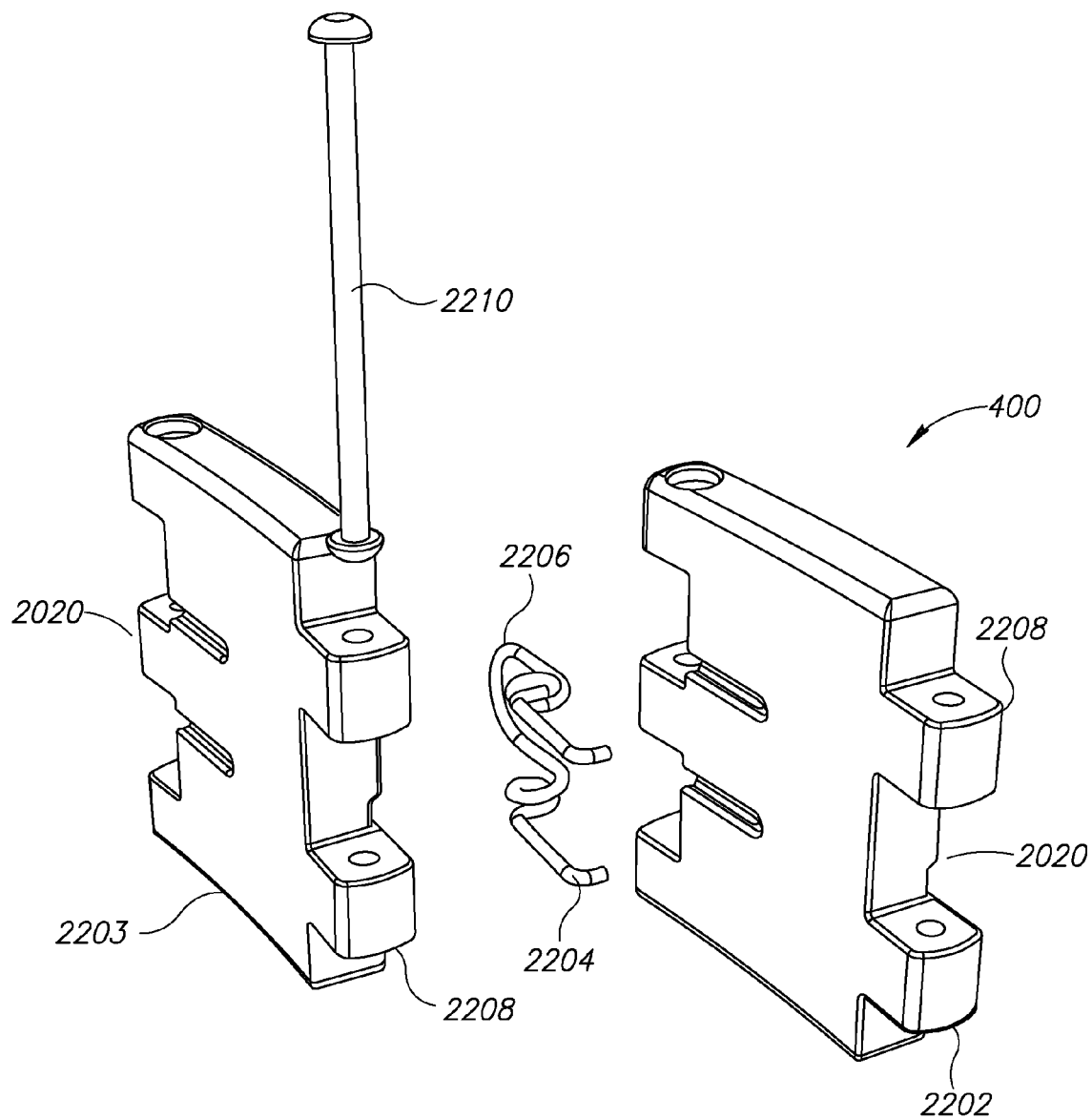

FIGS. 20-22 show details of two linked segments 2020, a left segment 2202 and a right segment 2203, which are connected through a non-limiting illustrative example of flexible connection 2204, in an exploded view (FIG. 20 is a front view, while FIG. 21 is a back view and FIG. 22 is the same as FIG. 21 but in a bit flatter view). Flexible connection 2204 preferably comprises a spring 2206, disposed therebetween and connecting left and right segments 2202 and 2203. Left and right segments 2202 and 2203 are also preferably connected at one side with at least one hinge 2208 and a connection pin 2210 which is inserted through hinge 2208 (not shown), for pivotably connecting segments 2202 and 2203. Spring 2206 between linked segments 2020 causes the arms 2002 and 2003 of pelvic anchor brace 400 to move radially inward, to help ensure a contour for each user as well as a snug fit, while still providing flexibility. In addition to the flexible movement, springs 2206 serve to exert a directional force between linked segments 2020, causing the arms (not shown) to conform to the body of the user. All of springs 2206 combined also serve to exert the pressure needed across the body, most importantly, between the posterior part-lumbar spine and sacrum and the anterior part—the ASIS (not shown).

The motion of at least some linked segments 2020 may be limited by stoppers or other limiting mechanisms, not shown. As shown, linked segments 2020 preferably have flexibility along the transverse plane. Additionally or alternatively, linked segments 2020 may optionally be designed to have flexibility in one or more other planes as well.

Springs 2206 between linked segments 2020 may optionally be of single springiness throughout arms 2002 and 2003. Alternatively, a first section of an arm 2002 or 2003 may optionally be manufactured with springs 2206 having a first level of springiness, and a second section of an arm 2002 or 2003 may optionally be manufactured with springs 2206 having a second level of springiness (not shown). In still further embodiments a plurality of different levels of springiness are included a plurality of different springs (not shown). By changing one or more areas of springiness, the overall dynamics of the arms 2002 and 2003 are preferably changed, for example optionally by changing the area where one arm exerts the most pressure.

Additionally changing one or more areas of springiness may enable easier donning or removal of pelvic anchor brace 400.

As in pelvic anchor brace 100 or 300, pelvic anchor brace 400 may include optionally removable attachments; for example snap-on straps or slots for a cell phone or a change purse or pouch, which may optionally be attached in any suitable manner, for example with glue, Velcro or any other type of attachment.

Additionally, one or more of linked segments 2020 may optionally be manufactured in different lengths so that by exchanging one or more links, the overall size and/or contour of pelvic anchor brace 400 can be changed (not shown).

Alternatively, one or more linked segments 2020 may optionally include two pieces that slide past each other, so that the length of each linked segment 2020 can be adjusted (not shown). In this manner, the overall size and/or contour of pelvic anchor brace 400 may be adjusted as well.

In further embodiments, a first linked segment 2020 may optionally be connected to a second linked segment 2020 by more than one hinge 2208 and/or more than one spring 2206. Further, spring 2206 may optionally be manufactured to have different shapes, for example a round or flat shape.

Additionally, one or more linked segments 2020 may optionally comprise a balloon portion which, for example, embraces the user more snugly upon inflation (not shown).

Additionally or alternatively, balloons can optionally be inserted between the linked segments 2020 so that when inflated they push linked segments 2020, acting like spring elements (not shown). The inserted balloons may optionally be in addition to, or instead of, the springs 2206 that connect linked segments 2020.

Additionally, further configurations may comprise flexible links, where the links themselves have inherent springiness. In using flexible links, there would again be an option to have no springs in the connections between the links (not shown).

In still further configurations, a first portion of links have a first inter alia, color, shape, flexibility, and/or material, while a second portion of links have a different color, shape, flexibility, and/or material. Further, this option may be extended to more than two portions of links.

FIG. 23A-E shows several optional embodiments according to the present invention for a spinal support 2500 as optional embodiments to spinal support depicted in FIGS. 1-22, providing support to the sacral region and the lordosis of the lumbar spine. Spinal support 2500, comprises at least one upper cushion 2510, at least one lower cushion 2512 and a plurality of optional joining axis 2502, 2504, 2506, 2508, 2520. Most preferably lower cushion 2512 provides support to the sacral region, while preferably upper cushion 2510 provides support to the lumbar spine. Most preferably, the cushions apply a controllable force to the sacral and lumbar spine therein providing support to the respective regions.

Optionally, joining axis 2502, 2504, 2506, 2508, 2520 may be provided in a plurality of forms for linking upper cushion 2510 and lower cushion 2512, for example including but not limited to a straight joining axis 2502 as is depicted in FIG. 23A, FIG. 23B depicts joining axis 2504 having convex shape. FIG. 23C depicts joining axis 2506 having an angled shape. FIG. 23D depicts joining axis 2508 having a spring like shaped joining axis. FIG. 23E depicts joining axis 2520 as an optional spring like shaped axis to that depicted in FIG. 23D. Joining axis 2502, 2504, 2506, 2508, 2520 is made of materials as is known and accepted in the art that for example including, metals, metal hybrids, plastic, plastic hybrids, composite materials, or the like. Preferably joining axis 2502, 2504, 2506, 2508, or 2520 is made of durable, pliable material that may be controllably flexible and/or rigid according to the support required. FIG. 23D showing axis 2508 is optionally constructed of a springy material such as spring steel ASTM A228, Stainless steel type302, Urethane, PVC or similar materials, bent into a springy shape during production.

Spinal support 2500 of FIG. 23 depicts an spinal support having optional forms of a joining axes 2502, 2504, 2506, 2508 and 2520 optionally having a predetermined length defining distance between upper cushion 2510 and lower cushion 2512. An optional embodiment of the present invention provides for a joining axis having a controllable distance between the upper and lower cushions. FIG. 24A-B depicts an optional embodiment of spinal support 2600 comprising an adjustable joining axis where most preferably the distance between upper cushion 2610 and lower cushion 2612 is controllable, and preferably determined by a user, physician or practitioner preferably in accordance with at least one or more parameters for example including but not limited to user anatomy, comfort or the like. FIG. 24A depicts the axis 2602 whose length is most preferably controllably increased and/or decreased along its axis to form joining axis 2604 of FIG. 24B that in turn change the cushion distance between upper cushion 2610 and lower cushion 2612. Optionally, the length of joining axis 2602 and 2604 may be controlled in a number of methods as is known and accepted in the art for example including but not limited to an adjustable joint, telescopic, ratchet, motorized, threading, lock and key, nut and bolt, folding, friction, folding links and others.

FIG. 25A shows an optional embodiment of the spinal support of the present invention further comprising a pivotal joint 2700 positioned along joining axis 2702 spanning the length between upper cushion 2710 and lower cushion 2712. Optionally and preferably, pivotal joint 2700 provides control of the angle and positions of upper cushion 2710 relative to the position of lower cushion 2712, as well as the distance between cushions 2710 and 2712. Optionally, pivotal joint provides full range of motion for example up to about 360 degrees in at least one and more preferably a plurality of planes of joining axis 2702.

Most preferably, cushions 2710 and 2712 apply pressure to the sacral and lumbar areas which is countered by the pivotal joint 2700. Pivotal joint 2700 is optionally and preferably securely coupled and fluidly connected to the axis 2702.

For example, if the total force applied is X (in a direction perpendicular to an imaginary straight line along axis 2702 connecting the cushions 2710 and 2712, then both cushions together will jointly apply force X. If we mark the forces applied by the cushions as force X1 for cushion 2710 and force X2 for cushion 2712 respectively and the distance of the upper cushion 2710 from the pivot joint 2700 as L1 and the distance of the lower cushion 2712 from the pivotal joint 2700 as L2, then the following is approximately true—

$$X1+X2=X \quad \text{(a)}$$

$$X1 \cdot L1 = X2 \cdot L2 \quad \text{(b)}$$

Equation (b) is true because the moments relative to the pivotal joint 2700 must cancel each other so that there is no movement.

Looking at the equations above, the different positions of axis provide an advantage in that when the pivotal joint 2700 is closer to one cushion, that cushion will apply a larger percentage of force X to the body and the other cushion will apply a smaller percentage of force X to the body. Adjusting the axis position enables control of the relative forces the cushions will apply on the body.

FIG. 25B shows a detailed close up view of an optional embodiment for coupling a cushion 2710 (it may be either the upper or lower cushion or both) where the cushion 2710 is connected to joining axis 2702 through a joint 2720, for example depicted as a ball and socket joint, however optionally realized in the form of a spring joint, static joint, a moveable joint, an manually adjustable joint, a self adjustable joint, a friction joint, a tension joint, a pressure or force based joint, a threaded locking joint, a locking joint, ratchet joint, motorized joint, nut and bolt, telescopic, or the like method for controllable coupling.

Figure 26:
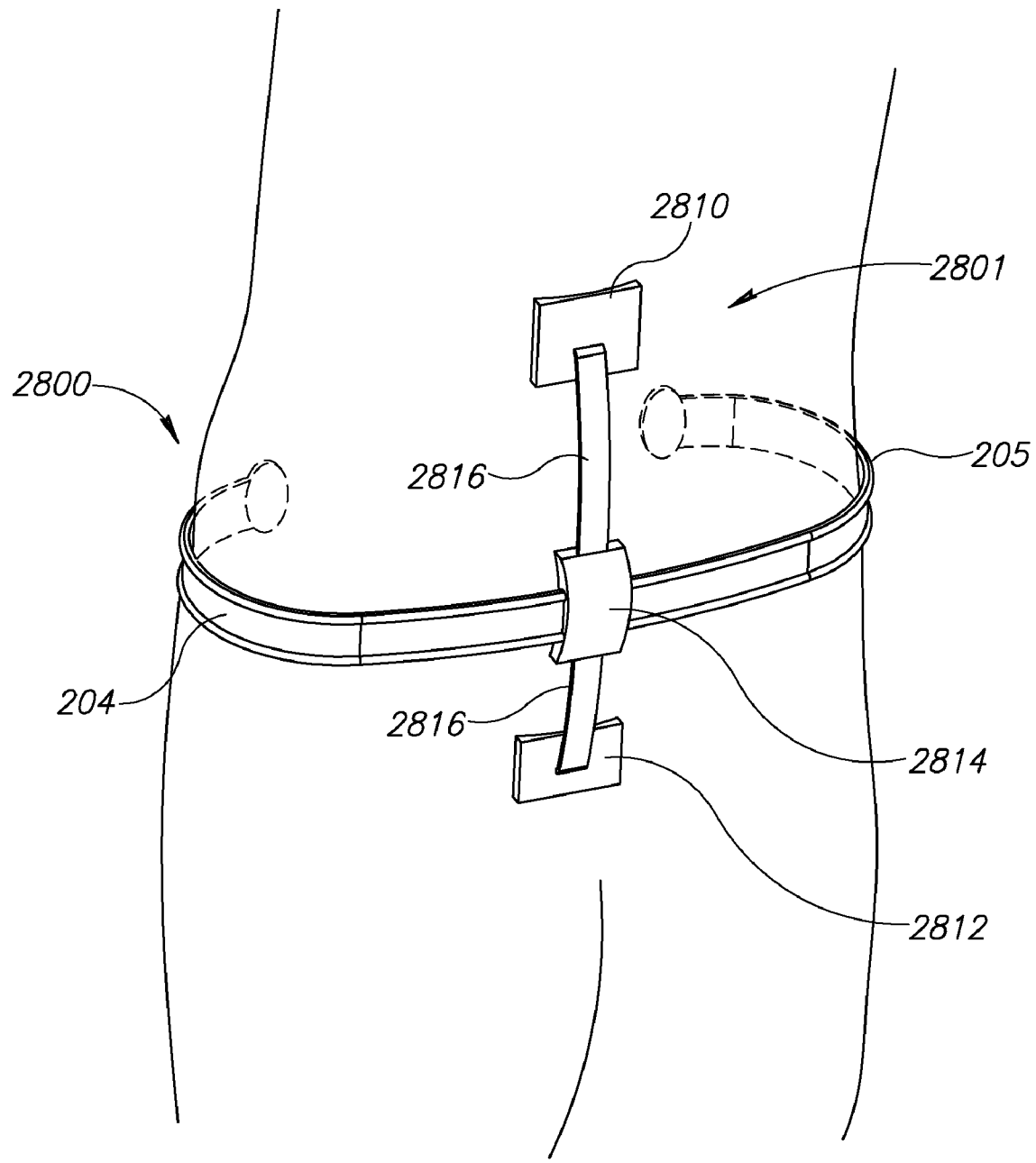
FIGS. 26-27 show optional assemblies of the spinal support according to a preferred embodiment of the present invention comprising a pivotal joint.

FIG. 26 shows a schematic and optional representation of a pelvic anchor brace 2800 comprising arms 204 and 205 as previously described above fitted with a spinal support 2801 such as that depicted in FIG. 25A. Pelvic anchor brace 2800 is preferably worn around the body of a user supported by the ASIS. Optionally, spinal support 2801 is integrated and provided with arms 204 and 205. Pelvic and spinal anchor 2801 comprises upper cushion 2810 and lower cushion 2812 mediated by joining axis 2816 through pivotal joint 2814.

Figure 27:
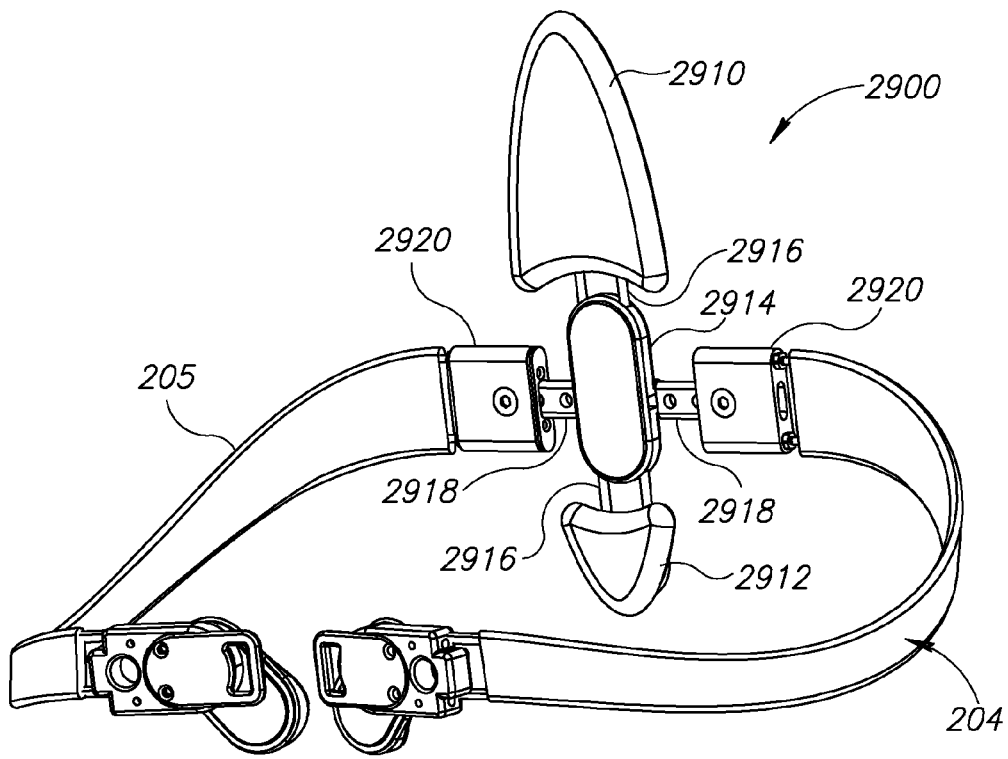

FIG. 27 shows a more detailed representation of the modular spinal support 2900 according to the present invention. Spinal support 2900 preferably comprises upper cushion 2910 and lower cushion 2912 that are mediated by axis 2916 through pivotal joint 2914. Optionally, arms 204 and 205 described above may be controllably and removably fixed to spinal support 2900 through pivotal joint 2914 along axis 2916 via coupling 2918 and 2920. Optionally, coupling 2918 and 2920 may be removed and fitted onto other waistline support structure, for example including but not limited to a belt, as shown in FIGS. 32-36. Optionally, spinal support may be coupled using a plurality of optional connectors for example including but not limited to snaps, buttons, buckles, zippers, hook and loop, nut and blot, screw or the like couplings as is known and accepted in the art.

Figure 28:
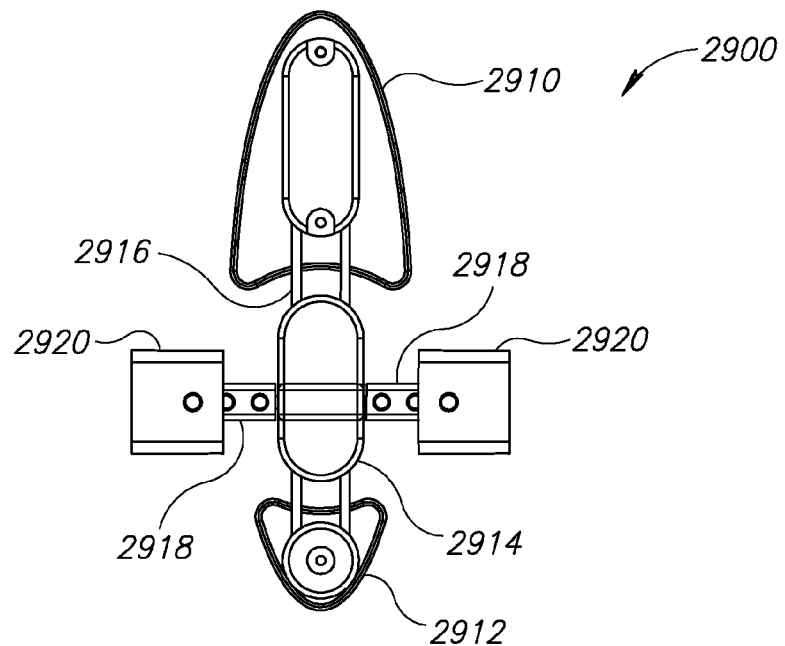
FIGS. 28-31 show close up views and exploded views of an optional embodiment of the spinal support according to a preferred embodiment of the present invention comprising a pivotal joint.

FIG. 28 depicts a back view of an optional embodiment of spinal support 2900 of FIG. 27. Optionally, cushions 2910 and 2912 are connected via joining axis 2916 optionally comprising 2 steel wires that preferably frictionally slide inside the pivot housing to set the axis position. Upper cushion 2910 can optionally slide along the two wires in order to adjust the distance between the cushions 2910 and 2912. Optionally, pivotal joint 2914 comprises several positions at which the couplings 2918 and 2920 may be disposed. Optionally and preferably couplings 2918 and 2920 are provided for coupling the spinal support according to the present invention to a plurality of optional attachments for example including but not limited to support belts, fashionable belts may be connected thereto. Optionally, coupling 2918 and 2920 may be realized in optional forms for example including ratchet as shown in FIG. 14, snaps, cogs, gear work, nut and bolt or the like as is known and accepted in the art.

Figure 29A:
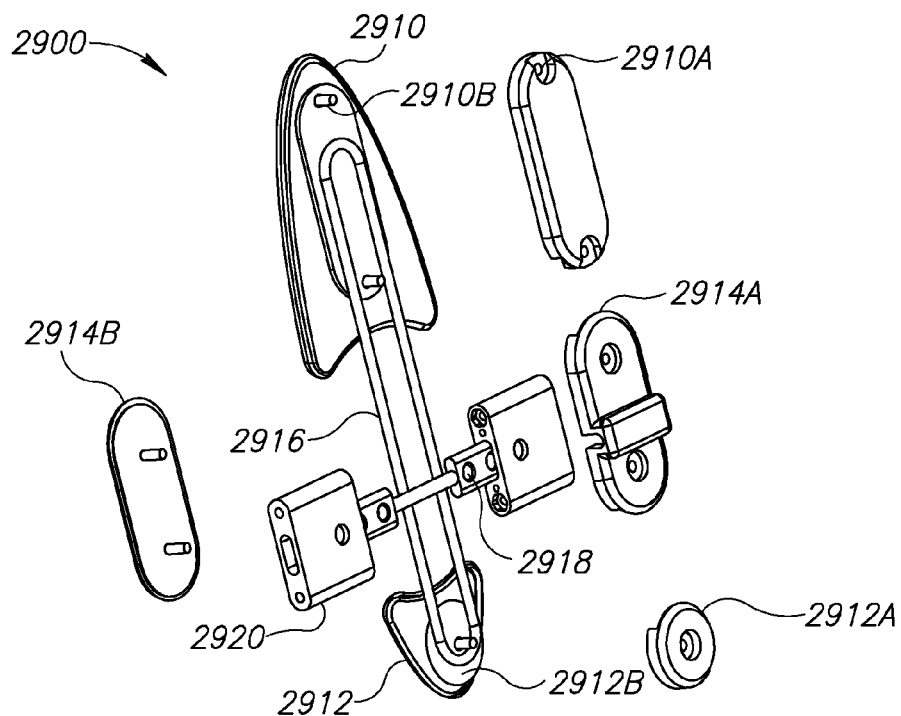
Figure 29B:
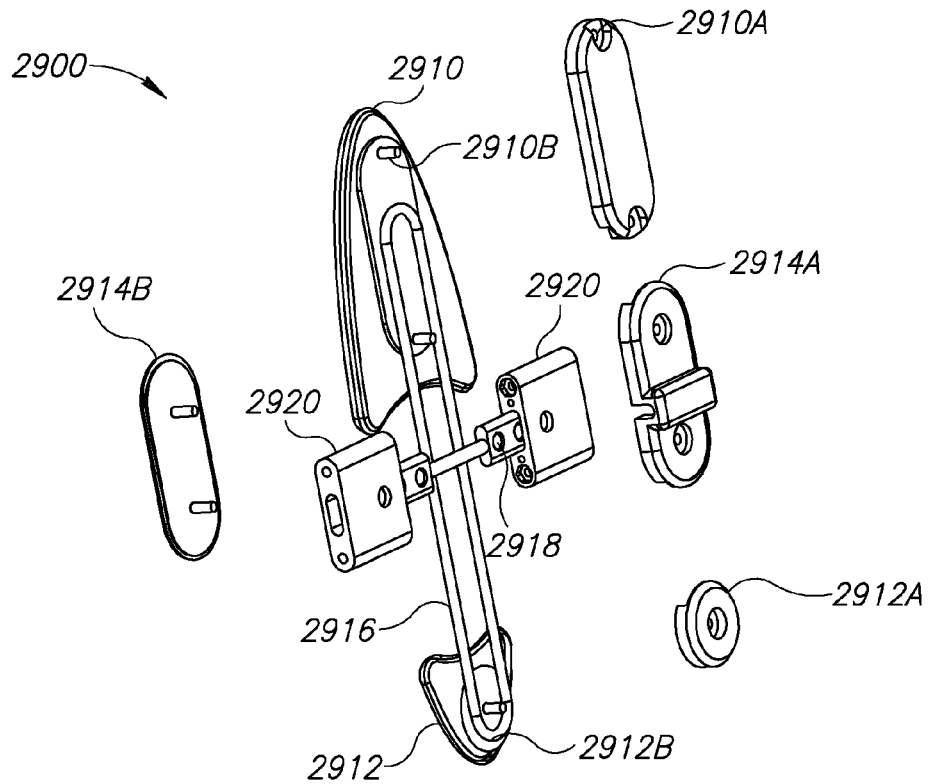

FIGS. 29A and 29B provides an alternate exploded views of spinal support 2900 as shown in FIGS. 27 and 28 therein showing the modular possibility of spinal support for accepting and utilizing a plurality of optional connector types for example including, ratchet, gear work, cogs, snaps, nut and bolt or the like as is known and accepted in the art. Optionally, coupling 2918 and 2920 comprising a horizontal axis of spinal support 2900 may be moved along the length of axis 2916 as shown couplings 2918 and 2920 are displaced along axis 2916 from a inferior position of FIG. 29A to a more superior position of FIG. 29B, optionally and preferably by sliding down axis 2916. As described above the move may be used by a user, physician or practitioner to provide a user with the appropriate amount of lumbar support, optionally by controlling the moment along axis 2916. Optionally, such adjustments are made with respect to at least one or more parameters for example including but not limited to user anatomy, comfort, force required in the lumbar region.

The modularity and control of spinal support 2900 is further shown by the provided exploded view where for example, couplings 2918 and 2920 may optionally be provided or exchanged with a coupling of a different form for example including but not limited to a ratchet, cog or the like, while still associated with joining axis 2916. For example, superior support member 2910 and inferior support member 2912 may be changed with an alternatively shaped support member to better fit a user while still using the same main axis 2916. For example, the locations of support member 2910 and/or 2912 may be controlled along the length of axis 2916 with different forms of couplers provided in the form of couplings 2910A and 2910B and 2912A and 2912B for example a clips and/or snaps may optionally be utilized.

Figure 30:
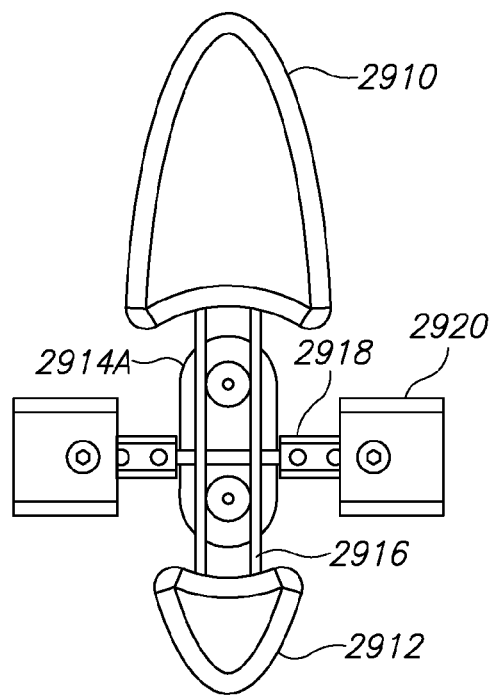

FIG. 30 provides a front partial cutaway view of spinal support 2900 of FIGS. 27 and 28 showing the cushions and joining axis from the front with the lid removed so that the axis positioning and pivot joint are visible. Most preferably cushions 2910 and 2912 may be positioned in accordance with at least one or more parameter for example including but not limited to anatomy or comfort. Optionally, cushions 2910 and 2912 may be positioned and/or fit by a user, practitioner or physician.

Figure 31:
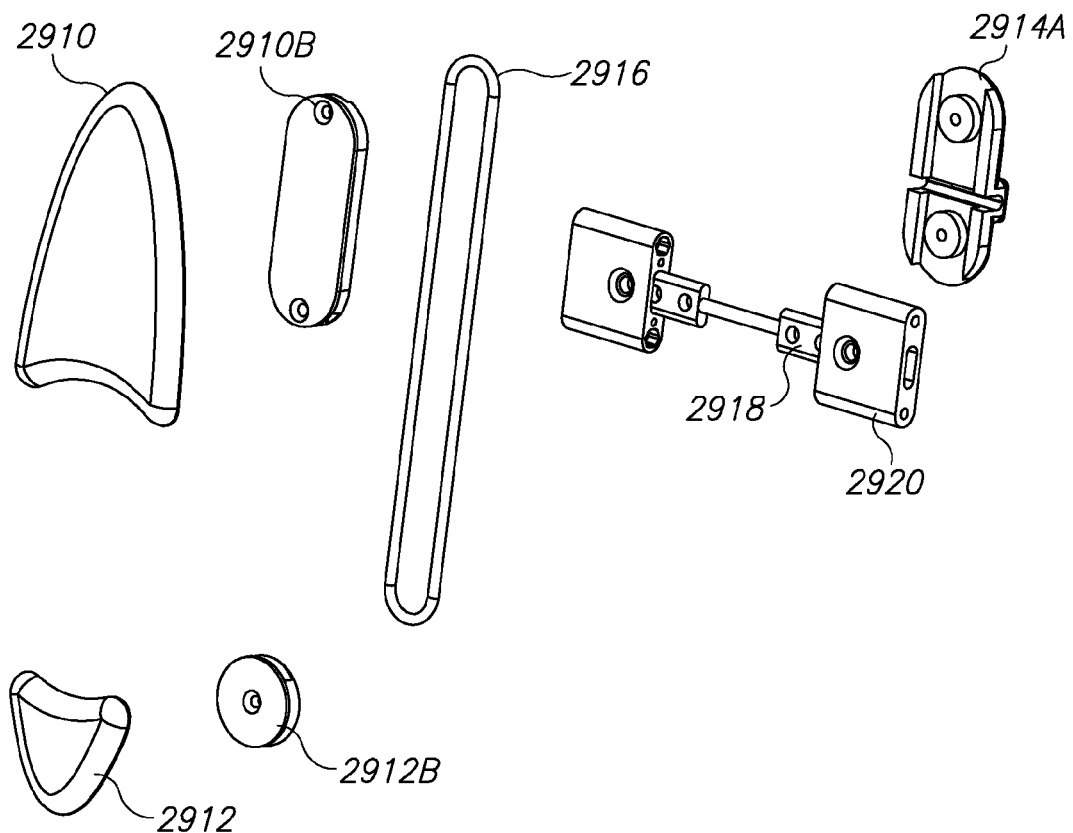

FIG. 31 shows a further exploded view of spinal support 2900 clearly depicting the various members comprising the spinal support 2900. Optionally and preferably, cushions 2910 and 2912 may be realized in a plurality of optional shapes, materials, texture, dimensions, pressure characteristics, heat characteristics, pliability, stiffness, color, smells or the like. Optionally, the parameters with which cushions 2910 and/or 2912 are provided may be determined by at least one or more parameters for example including but not limited to a user, a practitioner, a physician, or user's anatomy. Optionally and preferably a vertical axis is provided by axis 2916 while couplers 2918 and 2920 provide a horizontal axis and/or pivot. Most preferably, spinal support 2900 may be provided with a range of motion in both vertical and horizontal axes.

Optionally, cushions 2910 and 2912 may be provided with a treatment element (not shown) for example including but not limited to ultrasound, heat, cold, magnetic, laser, electrical current, TENS, biofeedback, RF, electromagnetic energy, optical or the like treatment element and or forms of energy.

Figure 32:
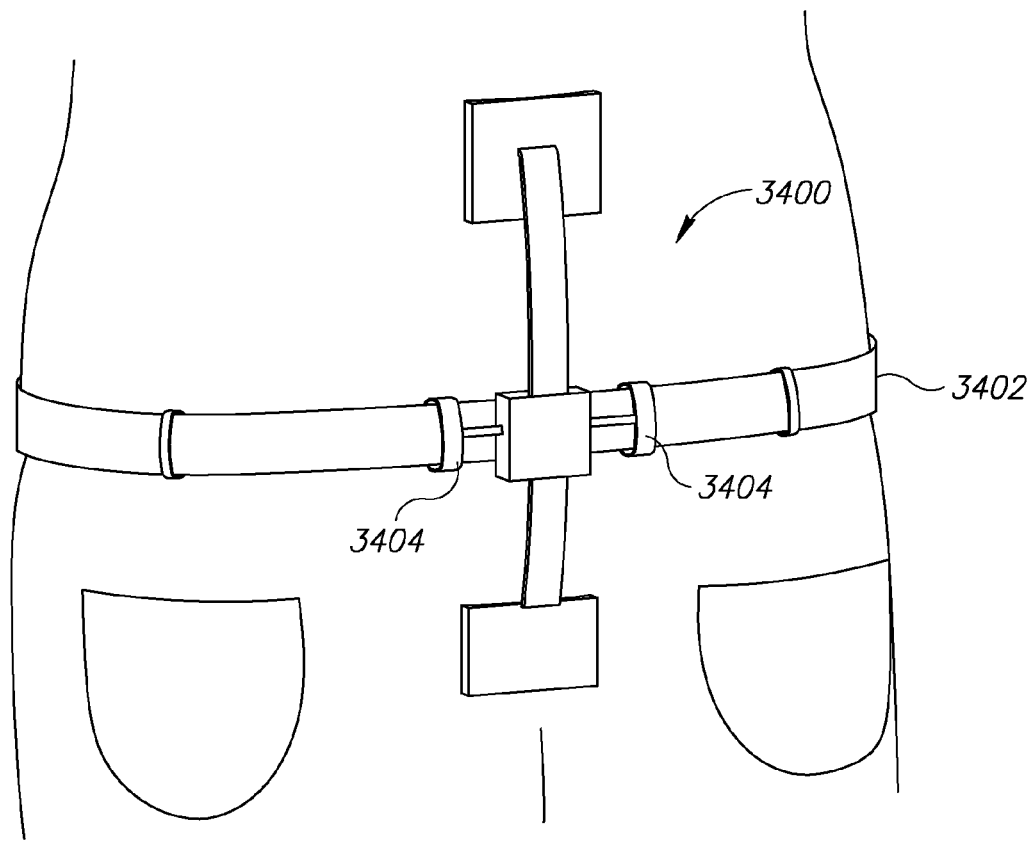
FIGS. 32-36 show the spinal support according to a preferable embodiment of the present invention in use with a plurality of standard waistline support devices.
Figure 33:
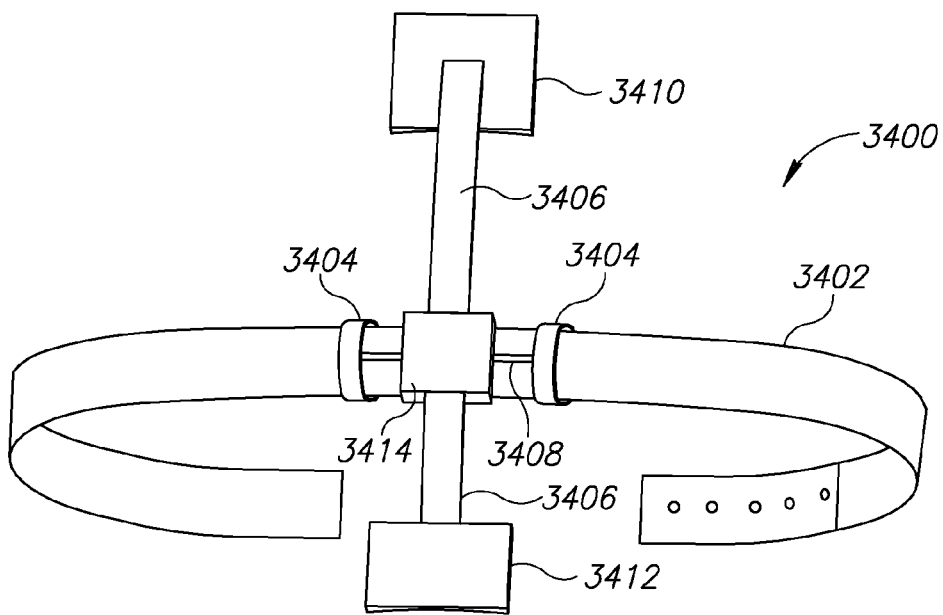
Figure 34:
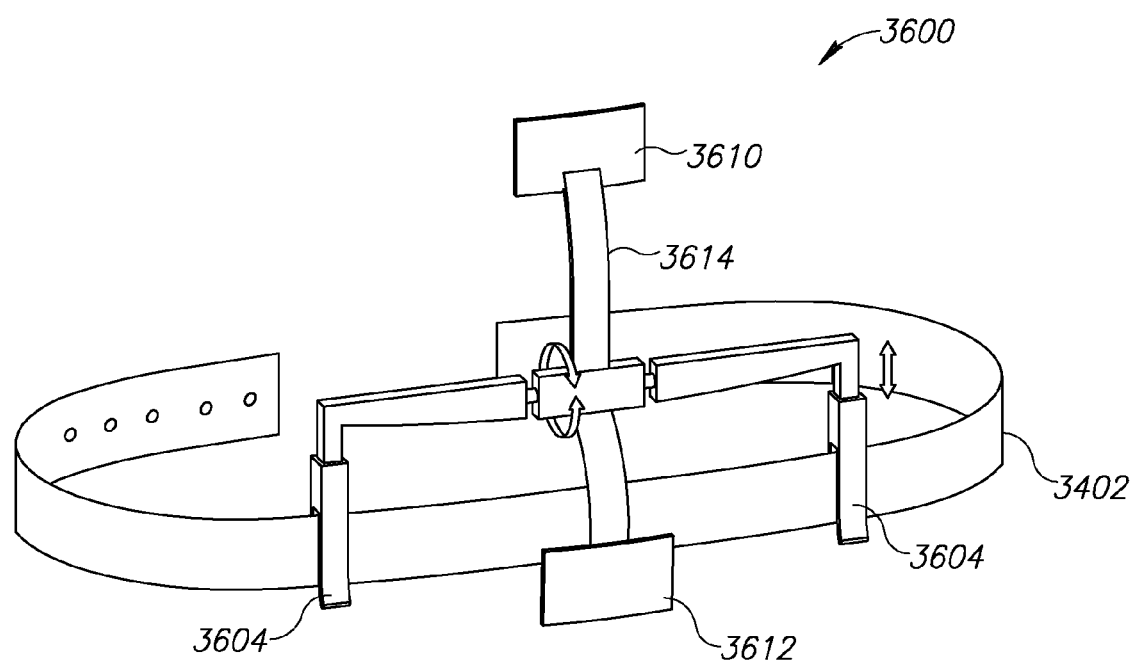
Figure 35:
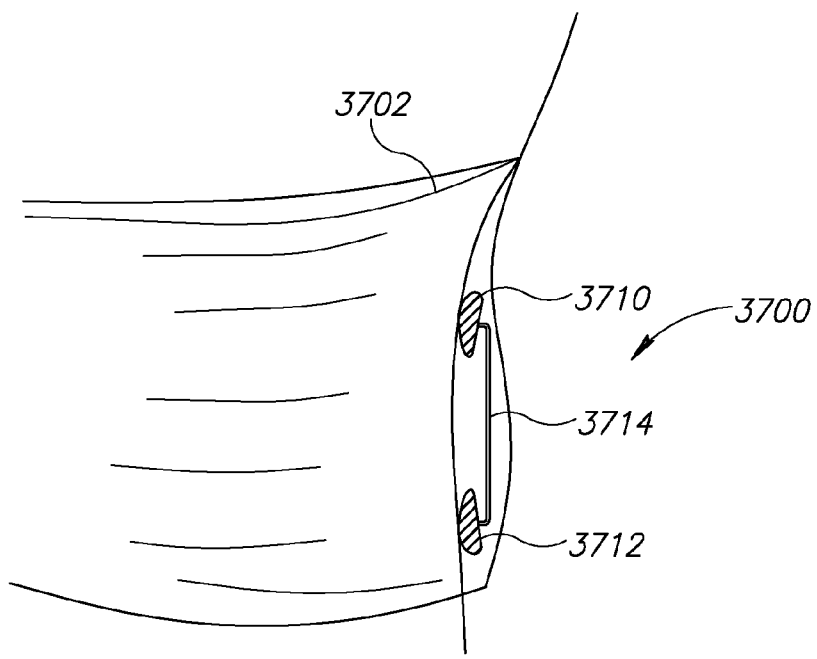
Figure 36:
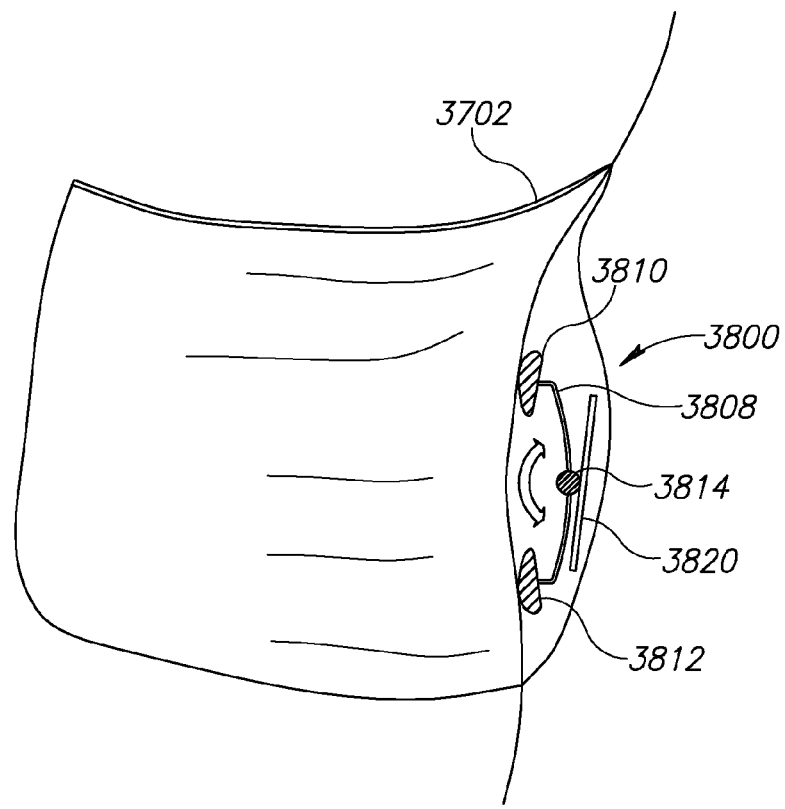

FIG. 32-34 shows a schematic depiction of optional spinal supports 200, 2500, 2600, and/or 2900 according to the present invention that may preferably be integrated into optional fashionable clothing item for example a waistline belt 3402 wherein spinal support 3400 is securely coupled thereto using optional couplings for example loops as shown in FIGS. 34 and 35, and clips as shown in FIG. 36, or the like couplings for example including but not limited to latch, buckle, snaps or the like. FIGS. 32-34 show use of spinal support 3400 in an optional external over cloths use while optionally under the cloth may similarly be provided. Optionally, spinal support 3400 may be provided wherein attachments may be to other article of clothing for example a pant, shirt or the like.

FIGS. 35 and 36 depict optional embodiments of the spinal support 3700 of the present invention in use with a motorcyclist wide belt. Optionally, spinal support may be integrated or more preferably controllably associated or disassociated with the motorcyclist wide belt 3702. FIG. 35 depicts anchor 3700 comprising upper cushion 3710 and lower cushion 3712 separated by joining axis 3714 in use within wide belt 3702.

FIG. 36 depicts anchor 3800 similar to anchor 3700 however further comprising pivotal joint 3814 and balance plate 3820. Preferably balance plate 3820 provides support and a platform to adjust and maintain the force exerted and support provided by cushions 3810 and 3812.

In still further options, pelvic anchor braces 100, 300, 400 and/or spinal support 200, 2500, 2600, 2800, 2900, 3400, 3600 and 3800 may be included in a kit featuring clothing having anchor buttons and/or hook and loop patches to which specially designed sections of the braces removably attach. The feature to attach a brace to clothing would benefit, for example, for a bike racer by preventing slippage of the brace during excessive movement.

It is expected that during the life of this patent many relevant supportive materials will be developed and the scope of the terms back brace and/or pelvic anchor brace are intended to include all such new technologies a priori.

As used herein the term "about" refers to ±10%.

EXAMPLES

Reference is now made to the following examples, which together with the above descriptions, illustrate the invention in a non-limiting fashion.

FIG. 11 shows a frontal view of an embodiment of pelvic anchor brace 100 being worn by a user.

FIG. 12 shows a side view of the embodiment of pelvic anchor brace 100 shown in FIG. 11.

FIG. 13 shows a close up of a side view of spinal support 200 shown in FIG. 12.

The user above wore the embodiment of pelvic anchor brace 100 shown in FIGS. 11-13 and was substantially relieved of lower back discomfort.

In addition, the inventors found that in certain cases, pelvic anchor brace 100 appears to present some advantages over lower back supports, noted in the summary, in that pelvic anchor brace 100 anchors on pelvic portions 232 and 233 which are substantially fixed in position and substantially unaffected by radially outward expansion of the abdomen during, for example, breathing.

In distinct contrast, U.S. Pat. Nos. 5,086,759 (Buddingh), and 5,551,085 (Leighton) and International Patent WO2004037135 (Weaver) comprise belts that entirely circle the user abdomen and are affected by outward radial changes during breathing, eating, and/or posture change.

Back supports that encircle the abdomen continually change position when the abdomen expands, for example after a meal, and thereby change their position and pressure on vertebra 262; which can be detrimental to user comfort and/or spinal therapy. Current back support belts are uncomfortable to users in transition, for example when changing from a sitting to a standing position, or vice versa, prior art back support belts tend to ride up or down the torso therein losing its effectiveness by primarily pressing or placing undue pressure on soft tissue.

Further it has been found that the pelvic anchor brace 100 according to the present invention comprising a spinal support 200 according to optional embodiments such as spinal support 200, 2500, 2600, 2900 provide an force optionally from about 2 kg to about 7 kg, optionally and preferably from about 2.5 kg to 5.5 kg and more preferably from about 3 kg to about 4 kg and most preferably form about 3 to about 3.5 kg of force. Most preferably this force is exerted on the lumbar lordosis, relieving lower back pain, relaxing tight muscles such as the psoas and reminding the user about posture and properly positioning the hips.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The present invention relates to a spinal and pelvic support belt configured to support and/or align one or more Lumbar vertebrae by providing a spinal and pelvic support belt that more closely resembles the pelvic anatomy allowing for use during daily activity without exerting undue pressure on the abdomen.

While the invention has been described with respect to a limited number of embodiments, it will be appreciated that many variations, modifications and other applications of the invention may be made.

What is claimed is:

1. A spinal support, comprising:
   (a) a right arm having an abutment that is adapted to abut against an anterior portion of the right pelvic bone; and
   (b) a left arm having an abutment that is adapted to abut against an anterior portion of the left pelvic bone; such that said abutment of said left arm is separated by a distance from said abutment of said right arm; wherein said right and left abutments are adapted to rest on said right and left anterior superior iliac spine, and (c) a posterior spinal support adapted to abut against at least a portion of the spine, comprising a connector for connecting each of said left and right arms to said posterior spinal support; wherein said right and left abutments are essentially on a plane parallel to said posterior spinal support, therein generating and exerting a force in an a posterior to anterior direction between said right and left abutments and said posterior support; wherein said right and left arm are configured to minimize pressure on the lateral sides of the body; wherein at least one of said abutment of said one right arm or said abutment of said one left arm adjustably extends with respect to said one posterior spinal support; wherein at least one of said one right arm or said one left arm are adjustable to assume at least two angles with respect to the longitudinal axis of said one posterior spinal support.

2. The spinal support according to claim 1, wherein said right arm and said left arm each include at least one synchronizing surface configured to synchronize movement between said one right arm and said one left arm.

3. The spinal support according to claim 2, wherein said at least one synchronizing surface is selected from the group consisting of a ratchet or cog.

4. The spinal support according to claim 1, wherein at least one of said one right arm; and said one left arm, comprises at least two segments that are rotatably connected.

5. The spinal support according of claim 1, including an alignment band that extends between said left arm and said right arm.

6. The spinal support according to claim 1, wherein said one right arm and said one left arm, comprise at least one resilient arm support.

7. The spinal support according to claim 1, including at least one removable covering.

8. The spinal support of claim 1 wherein said posterior spinal support, comprises:
   i) a superior padded member configured to press against at least one vertebra; and
   ii) an inferior padded member configured to press below said at least one vertebra.

9. The spinal support according to claim 8, wherein said one posterior spinal support is configured to be adjusted to press against said posterior portion of the spine with at least two levels of pressure.

10. The spinal support according to claim 8, wherein at least one of: said one superior padded member; and said one inferior padded member, are positionally adjustable with respect to said posterior spinal support.

11. The spinal support according to claim 10, wherein said one posterior spinal support includes a rigid backing; and said one superior padded member is juxtaposed against a compressible member that buttresses against at least a portion of said rigid backing.

12. The spinal support according to claim 11, wherein said compressible member comprises at least one of: a helical spring; and a pliant band.

13. The spinal support according to claim 11, wherein a portion of said one superior padded member is rotatably connected to a portion of said one inferior padded member.

14. The spinal support according to claim 11, wherein a portion of said one superior padded member is resiliently connected to a portion of said one inferior padded member.

15. The spinal support of claim 1 wherein said arms feature a gap between an end of each of said arms adapted to be placed in a proximal location to said anterior portion of the right and left pelvic bones.

16. The spinal support of claim 15, further comprising a non-supportive connector for connecting said end of each of said arms.

17. The spinal support of claim 1, wherein said connector further comprises an adjustable mechanism for providing one or both of pivotable and horizontally adjustable movements of said arms relative to said posterior spinal support.

18. The spinal support of claim 17, wherein said adjustable mechanism comprises a cogging mechanism for providing said pivotable movements.

19. The spinal support of claim 17, wherein said adjustable mechanism comprises a ratchet and a plurality of pegs for providing said horizontally adjustable movements of said arms.

20. The spinal support of claim 1 wherein said posterior-anterior force is exerted with a pressure force selected from about 2 kg to about 7 kg, or 2.5 kg to 5.5 kg, or 3 kg to about 4 kg.

21. A method for manufacturing a spinal support that anchors on a pelvis, comprising:
   i. making a posterior pad configured to support a portion of the spine;
   ii. extending a right arm anteriorly from said posterior pad such that a portion of said right arm is adapted to be butressed against an anterior portion of a pelvis about the right anterior superior iliac spine; and
   iii. extending a left arm anteriorly from said posterior pad such that a portion of said left arm is adapted to be butressed against an anterior portion of the pelvis about the left anterior superior iliac spine;
   wherein said right and left abutments are essentially on a plane parallel to said spinal support therein adapted for generating and exerting a force in a posterior to anterior direction between said right and left abutments and said posterior support;
   iv. curving said right arm so that said right arm is adapted to curve around at least a portion of a right pelvic bone;
   v. curving said left arm so that said left arm is adapted to curve around at least a portion of a left pelvic bone;
   vi. adapting said posterior pad to be adapted to provide a first pressure against said portion of the spine; and
   vii. adjusting a curvature of said right arm and said left arm to cause said posterior pad to be adapted to apply a second pressure against said portion of the spine.

22. A method for supporting a portion of a spine by generating and exerting a force in an a posterior to anterior direction, the method comprising:
   i. providing two curved arms extending from a posterior padded member, wherein said posterior padded member is adapted to support a portion of the spine;
   ii. placing an end of a first arm of said two curved arms so that said end is adapted to press against an anterior portion of the right pelvis about the right anterior superior iliac spine; and
   iii. placing an end of a second arm of said two curved arms so that said end is adapted to press against an anterior portion of the left pelvis about the left anterior superior iliac spine;
   iv. curving said first arm so that said first arm is adapted to curve around at least a portion of a right pelvic bone;
   v. curving said second arm so that said second arm is adapted to curve around at least a portion of a left pelvic bone;
   vi. causing said posterior padded member to be adapted to provide a first pressure against said portion of the spine; and
   vii. adjusting a curvature of said first arm and said second arm to cause said posterior padded member to be adapted to apply a second pressure against said portion of the spine.

23. The method according to claim 22, including:
   v) adapting said end of said first arm to be buttressed against said anterior portion of the right pelvis about the right anterior superior iliac spine; and
   vi) adapting said end of said first arm to be buttressed against said anterior portion of the left pelvis about the left anterior superior iliac spine.

24. The method according to claim 23, including: vii) adjusting the extension of at least one of said two curved arms with respect to said padded member.

* * * * *